Figure 2:
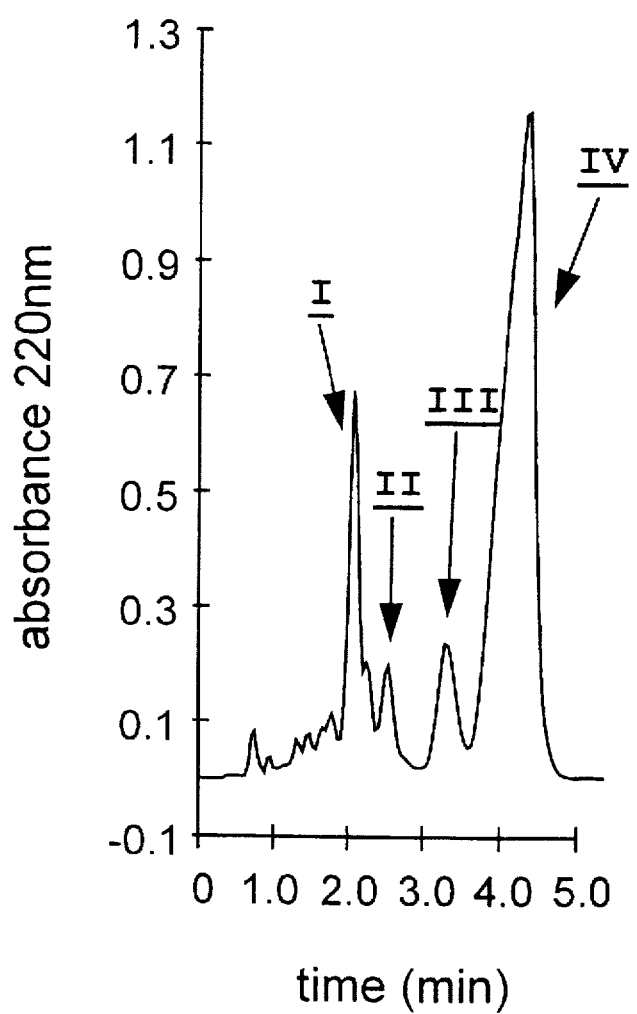

United States Patent [19]
VanDevanter et al.

[11] Patent Number: 5,767,068
[45] Date of Patent: Jun. 16, 1998

[54] PURE BIOLOGICALLY ACTIVE COLISTIN, ITS COMPONENTS AND A COLISTIN FORMULATION FOR TREATMENT OF PULMONARY INFECTIONS

[75] Inventors: Donald Robert VanDevanter. Puyallup; Alan Bruce Montgomery. Bellevue, both of Wash.

[73] Assignee: Pathogenesis Corporation. Seattle, Wash.

[21] Appl. No.: 799,300

[22] Filed: Feb. 13, 1997

[51] Int. Cl.$^6$ ............................ A61K 38/00; A61K 38/08; C07K 7/02; C07K 7/50
[52] U.S. Cl. .................................. 514/9; 514/11; 514/15; 530/317; 530/328
[58] Field of Search ............................ 514/9, 11, 15, 514/2; 530/317, 328

[56] References Cited

U.S. PATENT DOCUMENTS 5,091,365  2/1992  Sandow et al. .................. 514/9

FOREIGN PATENT DOCUMENTS

| | | |
|---|---|---|
| 2624738 | 6/1989 | France . |
| 51-00169 | 1/1976 | Japan . |
| 58-129993 | 3/1983 | Japan . |
| 59-067210 | 4/1984 | Japan . |
| 9600506 | 1/1996 | WIPO . |

OTHER PUBLICATIONS

Database Caplus, AN 1974:569819, Kurihara et al. Compounds related to colistin. akugaku Zasshi (1974), 94(9), 1183–7, Jan. 1984.

Newman et al. Efficient nebulization of powdered antibiotics. Int. J. Pharm. (Jan. 1987), 36(1), 55–60.

Elverdam et al. Isolation and characterization of three new polymyxins in polymixins B and E by high–performance liquid chromatography. J. Chromatography, 218, 653–661, Feb. 1981.

Kitamura–Matsunaga et al. A sodium containing polymixin derived from polymixin complex during chromatography. J. antiobiotics, 37(12), 1605–1610, Dec. 1984.

Kayaku Co., Ltd., Methacolimycin (Sodium Colistimethate), Tokyo, Japan. *Literatures on Methacolimycin Chemotherapy Against Urinary Tract and Intestinal Infections*, 1–49.

Kayaku Co., Ltd., Colimycin Injections Tablets, Tokyo, Japan, *Antibiotics Annual*, (1959–60).

J. Maddison, et al., Nebulized Colistin Causes Chest Tightness in Adults With Cystic Fibrosis. *Respiratory Medicine*, 145–147 (1994).

Yukio Kimura, et al., A Method For Separating Commercial Colistin Complex Into New Components: Colistins Pro–A, Pro–B and Pro–C. *The Journal of Antibiotics*, vol. XXXV No. 11, 1513–1520, (Nov. 1982).

John A. Bosso, et al., Research/Practice Reports, Toxicity of Colistin In Cystic Fibrosis Patients. *DICP, The Annals of Pharmacotherapy*, vol. 25, 1168–1170, (Nov. 1991).

A. A. Al–Khayyat, et al., Pharmacologic and Toxicologic Studies With The Polymyxins. *Chemotherapy*, 19:82–97, (1973).

Nebulised Colomycin For Early Pseudomonas Colonisation in Cystic Fibrosis, *The Lancet*, 865 (Apr. 13, 1985).

(List continued on next page.)

*Primary Examiner*—Cecilia J. Tsang
*Assistant Examiner*—Michael Borin
*Attorney, Agent, or Firm*—Hana Verny

[57] ABSTRACT

An anti-*Pseudomonas aeruginosa* agent which is substantially pure biologically active colistin, its component, a mixture thereof or a pharmaceutically acceptable salt thereof delivered as an aerosol or dry powder formulation. A formulation and method for preparation of substantially pure biologically active colistin, its components, mixtures thereof and a pharmaceutically acceptable salts thereof. A method for treatment and prophylaxis of *Pseudomonas aeruginosa, Stenotrophomonas maltophilia* or other susceptible pulmonary bacterial infections.

42 Claims, 20 Drawing Sheets colimycin     colistin (free base)

OTHER PUBLICATIONS

C. Vazquez, et al., Early Treatment of *Pseudomonas aeruginosa* Colonization in Cystic Fibrosis, *Acta Paediatr*, 82:308–9 (1993).

Margaret E. Hodson, MD, Msc, FRCP, DA., Cystic Fibrosis in Adolescents and Adults, *The Practitioner*, vol. 227, 1723–1731 (Nov. 1983).

Tim Jensen, et al., Colistin Inhalation Therapy in Cystic Fibrosis Patients With Chronic *Pseudomonas aeruginosa* Lung Infection, *Journal of Antimicrobial Chemotherapy*, 19, 831–838 (1987).

A. Bauernfeind, et al., Comparative Microbiological Effects of Combination Therapy With Ciprofloxacin Plus Colistin vs. Monotherapy With Ciprofloxacin or Colistin Against *Pseudomonas aeruginosa*, Abstracts, International Cystic Fibrosis Symposium (Sep. 26–28, 1996), *Monatsschr Kinderheilkd* 144:1028 & 1042 (1996).

Niels H. Valerius, et al., Prevention of Chronic *Pseudomonas aeruginosa* Colonisation in Cystic Fibrosis by Early Treatment, *The Lancet*, vol. 338, 725–726 (Sep. 21, 1991).

FIG. 1A
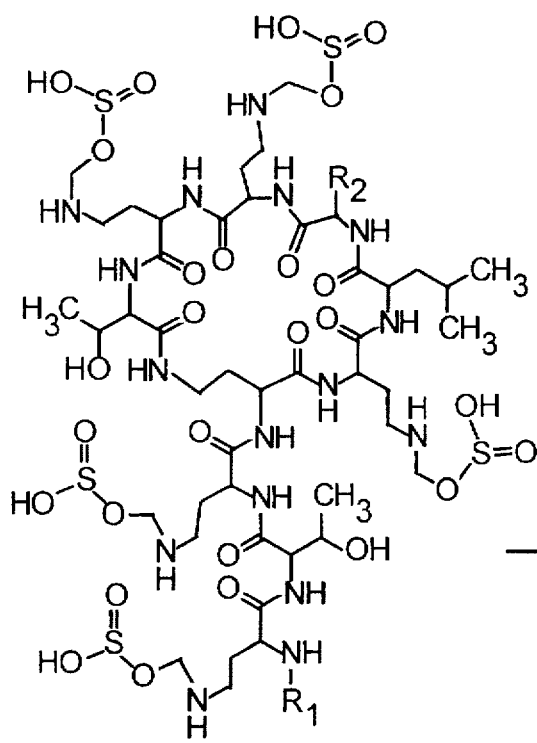
colimycin
FIG. 1B
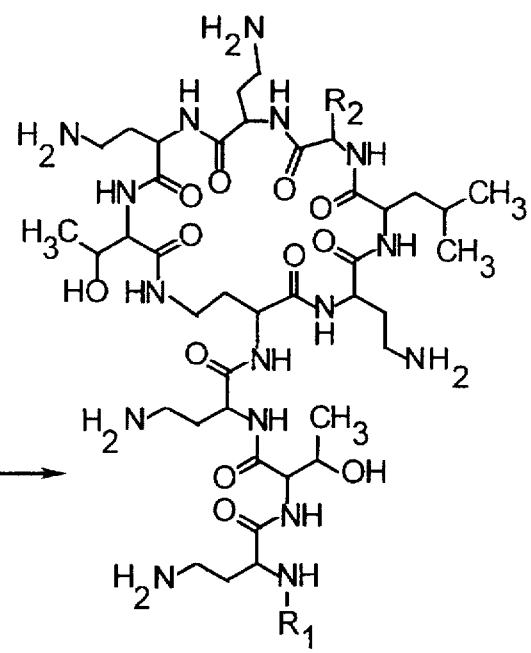
colistin (free base)
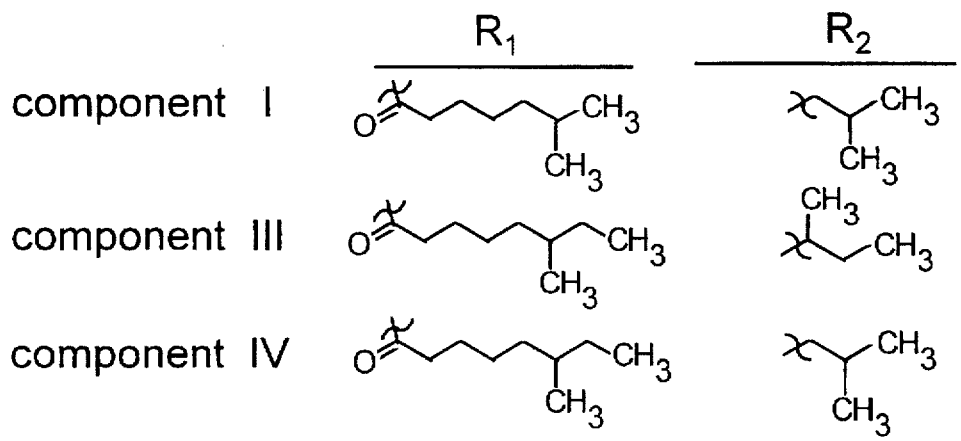

component I component III component IV

FIG. 7A  component I
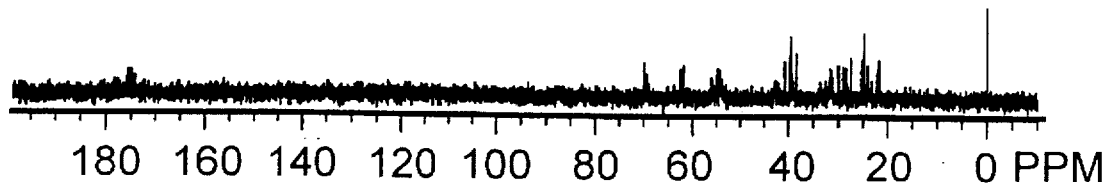
FIG. 7B  component III
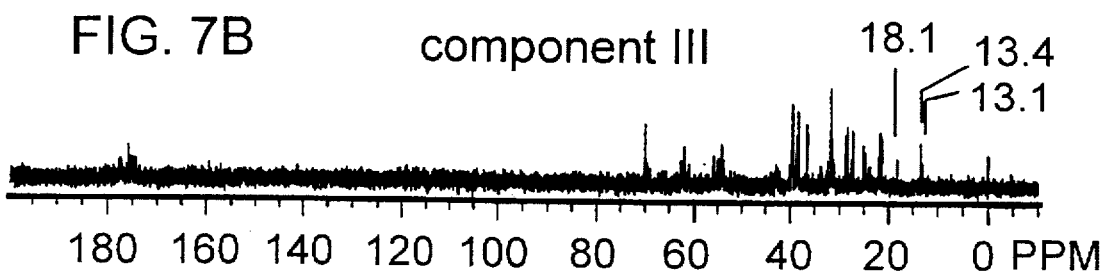
FIG. 7C  component IV
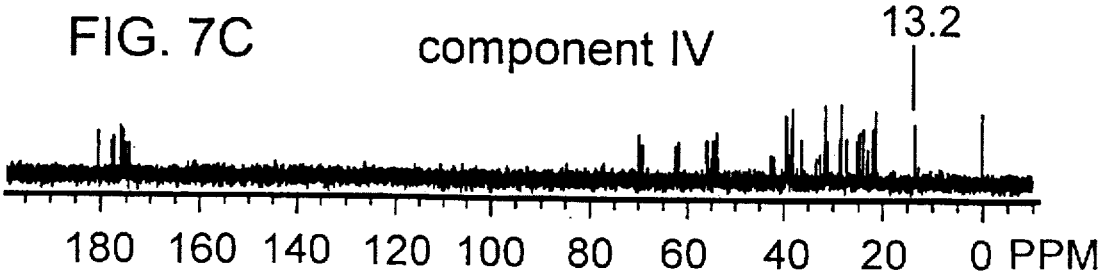

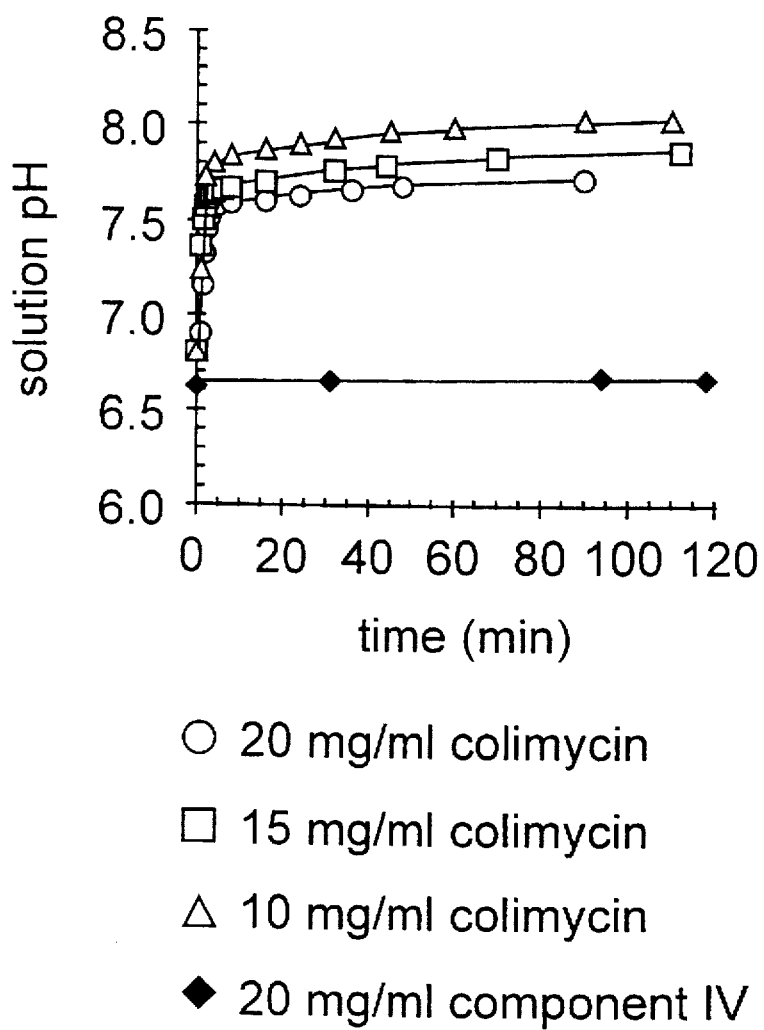

FIG. 18

PURE BIOLOGICALLY ACTIVE COLISTIN, ITS COMPONENTS AND A COLISTIN FORMULATION FOR TREATMENT OF PULMONARY INFECTIONS

This application is based on the provisional patent application Ser. No. 60/030,939, filed on Nov. 15, 1996.

BACKGROUND OF THE INVENTION

1. Field of Invention

The current invention concerns a pure biologically active colistin and all its components, any mixture thereof, and pharmaceutically acceptable salts thereof, as well as an aerosol formulation comprising a substantially pure biologically active colistin, any of its biologically active components, a mixture thereof or a pharmaceutically acceptable salt thereof. The formulation is suitable for nebulization and in its nebulized form provides an effective treatment and prophylaxis of *Pseudomonas aeruginosa* and other susceptible pulmonary infections such as *Stenotrophomonas maltophilia*. The pure colistin is devoid of impurities, has a standard high biological activity per weight of dry powder, a high temperature stability, and is suitable for aerosolization using jet or ultrasonic nebulizers as well as for delivery by dry powder or metered dose inhaler. The pure colistin has long-term stability permitting the formulation to be premixed and stored at room temperature.

The aerosol formulation comprises a concentrated solution of 0.1 to 50 mg/ml of pure colistin, any of its components or its pharmaceutically acceptable salt, dissolved in isotonic aqueous solution having a pH between 5.0 and 7.0. The therapeutic amount of the pure colistin is delivered to the lung endobronchial space by nebulization in an aerosol or dry powder having an average mass medium diameter between 1 to 5μ.

2. Background and Related Disclosures

Chronic pulmonary colonization with *Pseudomonas aeruginosa* in patients with cystic fibrosis is a principal cause of their high mortality. When established, the chronic pulmonary infection is very difficult, if not impossible, to eradicate. More than 60% of cystic fibrosis patients are colonized with *Pseudomonas aeruginosa* bacterium strains which are largely resistant to antibiotics, such as piperacillin, ticarcillin, meropenem, netilmicin and only little sensitive to azlocillin, ciprofloxacin, timentin, ceftazidime and aztreonam. Most strains of *Pseudomonas aeruginosa* have been shown to be sensitive to treatment with tobramycin (about 90%) and to colistin (about 98%).

Aerosolization of tobramycin has previously been attempted in cystic fibrosis patients to suppress *Pseudomonas aeruginosa* infections, decrease lung inflammation and improve lung function. Successful treatment of *P. aeruginosa* infection in cystic fibrosis with aerosolized tobramycin which has relatively high activity against the *P. aeruginosa* bacterium, is described in *Ped. Pulmonol.*, 7:265 (1989).

Colistin is a fermentation product consisting of at least four active components, all of which are characterized by the presence of a cyclic peptide moiety and five alkyl amines derived from gamma-diaminobutyric acid. The presence of these amines in an underivatized state is essential for biological activity against *Pseudomonas aeruginosa*. Colimycin is a prodrug form of colistin commonly used for intravenous and intramuscular injections to reduce pain at the site injection caused by colistin, and consists of penta formaldehyde sodium sulfite amine adducts of the colistin fermentation product. Colimycin is not itself biologically active and requires hydrolysis in aqueous solution to release active colistin, with formaldehyde and bisulfite formed as hydrolytic byproducts.

Previously, attempts were made to use the colistin prodrug colimycin against the *P. aeruginosa* pathogen. The treatments of *P. aeruginosa* infections by aerosolized colimycin, alone or in combination with other drugs or antibiotic treatments were not very successful. This is primarily due to the fact that colimycin itself is only a prodrug of colistin and as such is not an effective drug against *P. aeruginosa*. The administered amount of prodrug does not predict the therapeutic efficacy of colistin as the conversion of the prodrug colimycin to the drug colistin proceeds in situ and such conversion cannot be controlled. During its in situ conversion colimycin produces degradation byproducts leading, during its aerosol delivery, to development of secondary undesirable symptoms such as bronchoconstriction and chest tightness. Since colimycin is an unpurified fermentation product, it contains impurities.

Preventive use of nebulized colimycin (500,000 IU; 17 mg/twice day) for early Pseudomonas infections was described in *The Lancet*, 1(8433): 865, (1985). While this treatment indicated a reduced number of Pseudomonas organisms, significant bronchospasm was observed following the delivery of nebulized colimycin.

Combined treatment of *P. aueruginosa* described in *Acta Pediatr.*, 82:308 (1993) involved the administration of systemic ciprofloxacin and the aerosolized mixture of colimycin/tobramycin (1,000,000 IU; 33mg/100 mg, respectively) twice daily. This therapy resulted in delay of the onset of *P. aeruginosa* in cystic fibrosis patients.

In a separate study, patients treated with systemic or aerosolized colimycin also reported undesirable secondary symptoms. For example, *Resp. Med.*, 88:145 (1994) describes a development of bronchoconstriction response reported as chest tightness by approximately 65% of patients treated with 2,000,000 units of nebulized colimycin. Systemic intravenous treatment of cystic fibrosis patients with a diagnosis of acute pulmonary exacerbation with colimycin resulted in occurrence of neurotoxicity symptoms in about 29% cases and in nephrotoxicity symptoms in about 5% cases (*DICP, Ann. Pharmacother.*, 25:1168 (1991)).

Partial prevention of chronic *P. aeruginosa* colonization was reported in *The Lancet*, 338:725 (1991) following the early treatment of patients with combination treatment of oral ciproflaxin (1,000,000 IU) and inhalation of colimycin twice daily for three weeks.

The latest publication on the subject of treatment of *P. aeruginosa* appears as abstract P12, in *Abstracts, International Cystic Fibrosis Symposium*. p. 1042, Sep. 26–28, 1996, published in *Monatsschr. Kinderheilkd*, 144:1028–1051 (1996). The paper compares effects of combination ciproflaxin/colimycin therapy to monotherapy with each agent individually. These studies show that combination of oral ciproflaxin with inhaled colimycin was more than five times more effective than aerosol colimycin therapy alone.

Thus, existing colimycin treatments and formulations for treatment and prevention of *P. aeruginosa* pulmonary infections are either ineffective, unpredictable, uncontrollable, cause undesirable secondary symptoms, must be combined with other treatments, or need very large amounts of the drug which amounts are difficult to nebulize.

From the brief description above, it is clear that there is a continuous need for an effective therapy of *P. aeruginosa* infections. Such therapy should preferably be delivered by inhalation of the aerosolized therapeutically effective drug formulation directly to the lung to avoid systemic treatment.

Such effective aerosol administration is, however, currently compromised by the lack of stable, efficient and physiologically balanced formulations and also by the inability of certain nebulizers to nebulize therapeutic quantities of colimycin into small and uniform particle size aerosols. A range of aerosolized particles needed to deliver the drug to the endobronchial space, the site of the infection, is between 1–5μ. Many nebulizers which could aerosolize large therapeutic volumes of colimycin produce large number of aerosol particles in the range of 50–100μ. In order to be therapeutically effective, the majority of aerosolized colistin particles should not have larger mass medium average diameter (MMAD) than between 1 and 5μ. When the aerosol contains a large number of particles with a MMAD larger than 5μ, these are deposited in the upper airways decreasing the amount of antibiotic delivered to the site of infection in the lower respiratory tract.

Currently, two types of available nebulizers, jet and ultrasonic, can produce and deliver aerosol particles having sizes between 1 and 5μ. These particle size are optimal for treatment of *Pseudomonas aeruginosa* infections. However, large volumes of this drug needs to be administered to obtain a therapeutic effect and, therefore, the efficient delivery of colimycin is not possible. These nebulizers are unable to deliver colimycin in any efficient manner because the high concentrations of colimycin required for biological activity cause foaming during aerosolization, thereby preventing the efficient delivery of the drug.

Additionally, when the prodrug colimycin is used for aerosolization, in order to be therapeutically effective, the inactive prodrug must first be converted to the active drug colistin. Such conversion proceeds in situ and is quantitatively unpredictable. Additionally, the pH of aqueous colimycin quickly rises to non-physiologic levels, and formaldehyde and other byproducts are formed during prodrug hydrolysis, both of which induce bronchospasm, an unwanted occurrence in patients with lung diseases such as cystic fibrosis.

Thus it would be advantageous to provide an aerosol formulation of active colistin able to control *P. aeruginosa* or other bacterial pulmonary infections both therapeutically and preventively, said colistin formulation containing solely the active components of colistin, or a single active component or a mixture thereof, wherein the drug has a standard activity and increased biological activity per gram of dry weight, wherein pH is adjusted to physiologically acceptable levels, which formulation has adequate shelf life suitable for commercial distribution, storage and use.

It is, therefore, a primary object of this invention to provide a concentrated formulation of substantially pure colistin or/and colistin active component or a mixture thereof, or a pharmaceutically acceptable salt thereof, which contains sufficient but not excessive concentration of the active drug without the presence of the prodrug, which formulation can be efficiently aerosolized by nebulization using jet and ultrasonic nebulizers, into an aerosol having particle sizes within a range from 1 to 5μ, which formulation is designed to permit generation of a colistin aerosol well tolerated by cystic fibrosis patients, which formulation additionally has an adequate shelf life.

A formulation potency, on a mass basis, allows alternative delivery of colistin as a dry powder using dry powder or a metered dose inhaler. A sufficiently potent formulation of pure colistin, colistin component, a mixture thereof, or a pharmaceutically acceptable salt provides a dry powder advantageously used for dry powder or metered dose inhalation of drug particles milled to particle sizes within a range of 1 to 5 microns. The dry powder formulation is convenient because it does not require any dilution, it has an extended shelf-life and the inhalation delivery devices are portable and do not require an air compressor needed by nebulizers.

All patents, patent applications and publications cited herein are hereby incorporated by reference.

SUMMARY

One aspect of the current invention is a substantially pure colistin, any of its biologically active components, a mixture thereof or a pharmaceutically acceptable salt thereof.

Another aspect of the current invention is a substantially pure biologically active component of colistin sulfate identified as colistin component I, III or IV which component is a product of fermentation of bacteria *Bacillus polymyxa* or *Bacillus polyaerogenus* used as an active compound for aerosolized treatment of pulmonary *Pseudomonas aeruginosa* infections.

Another aspect of the current invention is an aerosol formulation of a substantially pure biologically active colistin, a colistin component, a mixture thereof or a pharmaceutically acceptable salt thereof, suitable for efficacious delivery of colistin into the endobronchial space of a patient suffering from cystic fibrosis.

Still another aspect of the current invention is an aerosol formulation comprising from about 1–50 mg of substantially pure biologically active colistin, a colistin component, mixture thereof or a pharmaceutically acceptable salt thereof, in about 1 ml of saline ranging from a half to a full strength or other aqueous solvent, wherein said formulation has a pH between 5.0 and 7.0 and is delivered in about 2–5 ml concentrated form by aerosolization.

Still another aspect of the current invention is a formulation comprising from about 1–50 mg of substantially pure biologically active colistin, a colistin component, a mixture thereof or a pharmaceutically acceptable salt thereof, dissolved in about 1 ml of saline ranging from a half to a full strength or other aqueous solvent, wherein said formulation has a pH between 5.0 and 7.0 and is delivered in about 2–5 ml of solution containing about 5–250 mg of pure colistin in aerosol particles having the mass medium average diameter predominantly between 1 and 5μ, wherein said formulation is nebulized using a jet or ultrasonic nebulizer.

Still another aspect of the current invention is a formulation comprising from about 1–50 mg of substantially pure biologically active colistin, a colistin component, a mixture thereof or a pharmaceutically acceptable salt thereof, wherein said formulation is milled to a fine powder, having particles with the mass medium average diameter between 1 and 5μ, used for administration by dry powder or metered dose inhalers.

Still yet another aspect of the current invention is a method for producing a purified colistin, any of its components, a mixture thereof or a pharmaceutically acceptable salt thereof using high performance liquid chromatography or other suitable methods.

Still another aspect of the current invention is a method for treatment of *Pseudomonas aeruginosa* infections or other susceptible bacterial infection such as *Stenotrophomonas maltophilia* by administering to a subject requiring such treatment a formulation comprising 1–50 mg of substantially pure biologically active colistin, a colistin component or a pharmaceutically acceptable salt thereof in 1 ml of a full or half strength saline or an aqueous solution wherein said formulation has a pH between 5.0 and 7.0 and is delivered by a jet or ultrasonic nebulizer in 2–5 ml concentrated form in an aerosol producing a particle size having the mass medium average diameter predominantly between 1 and 5μ.

Still another aspect of the current invention is a method for treatment of *Pseudomonas aeruginosa* infections or other susceptible bacterial infections such as *Stenotrophomonas maltophilia* by administering to a subject requiring such treatment a formulation comprising 1–50 mg of substantially pure biologically active colistin, a colistin component or a pharmaceutically acceptable salt thereof, wherein said formulation is milled to a fine powder with particles having a mass medium average diameter between 1 and 5μ and is delivered by dry powder or metered dose inhaler.

DEFINITIONS

As used herein:

"Colimycin", "colistimethane", "coly-mycin", "colistin methane sulfate", "colistin sulfomethane sodium", "totazina", "colomycin", "coliracin", "colomycine", "colimicina", "kolismetin", "methacolimycin" or "colisticine" means a bactericidal cyclopolypeptide antibiotic produced by *Bacillus polyaerogenus, Bacillus colistinus* or *Bacillus polymyxa,* which is a chemically derived prodrug of a biologically active colistin. The prodrug colimycin is converted in situ into the active drug colistin. Colimycin has a general formula seen in FIG. 1A.

"Pure colistin", "pure biologically active colistin" means an active drug colistin having a general formula seen in FIG. 1B, wherein the R is substituted as shown and ordinarily contains a mixture of all colistin components.

"Colistin component" or "colistin fraction" means a component or a fraction isolated from a fermentation product of *Bacillus polymyxa* or *Bacillus polyaerogenus* and separated by high performance liquid chromatography or by other separation means into individually chemically and physically identifiable fractions represented by components identified as colistin component I, II, III, IV, etc. Each of these components represents a different R substituent as seen in FIG. 1B. Other components obtained from the same fermentation product are also included in this definition.

"Colonization" means the presence of bacterium *Pseudomonas aeruginosa* within the lumen of the respiratory tract. Typically, the bacterium is isolated from sputum cultures and from throat swabs.

"Substantially pure" or "substantial purity" means more than 90% pure, biologically active chemical entity isolated and purified from the fermentation product of *Bacillus polymyxa* or *Bacillus polyaerogenus*. The unpurified, approximately 70% active colistin is commercially available as colistin sulfate U.S.P.

"Pharmaceutically acceptable salts" means non-toxic salts of the compounds of this invention, namely colistin free base or colistin components, which are prepared by reacting the free base with a suitable organic or inorganic acid. Representative pharmaceutically acceptable salts are acetates, benzenesulfonates, benzoates, bicarbonates, bisulfates, bitartrates, borates, bromides, calcium edetates, camsylates, carbonates, chlorides, clavulanates, citrates, dihydrochlorides, edetates, edisylates, estolates, esylates, fumarates, gluceptates, gluconates, glutamates, glycollylarsanilates, hexylresorcinates, hydrabamines, hydrobromides, hydrochlorides, hydroxynaphthoates, iodides, isothionates, lactates, lactobionates, laurates, malates, maleates, mandelates, mesylates, methylbromides, methylnitrates, methylsulfates, mucates, napsylates, nitrates, oleates, oxalates, pamaotes, palmitates, panthothenates, phosphate/diphosphates, polygalacturonates, salicylates, stearates, subacetates, succinates, tannates, tartrates, teoclates, tosylates, triethiodides, valerates.

BRIEF DESCRIPTION OF DRAWINGS

FIG. 1 shows a general structure of a prodrug colimycin (FIG. 1A) and a generic formula of a drug colistin and its components substituents (FIG. 1B).

FIG. 2 shows a graph of a typical elution profile for analytical HPLC fractionation of colistin sulfate.

FIG. 3 is an HPLC profile of preparative fractionation of colistin components I, III and IV from colistin sulfate U.S.P.

FIG. 4 is a graph showing the extinction coefficient of colistin component IV.

FIG. 5 are graphs of UV absorbance spectra of colistin component, component I (FIG. 5A), colistin component III (FIG. 5B) and colistin component IV (FIG. 5C).

FIG. 6 are positive ion-spray mass spectra of colistin component I (FIG. 6A), colistin component III (FIG. 6B) and component IV (FIG. 6C).

FIG. 7 are $^{13}C$ NMR spectra of colistin component I (FIG. 7A), colistin component III (FIG. 7B) and colistin component IV (FIG. 7C).

FIG. 8 is a comparison of relative anti-*Pseudomonas aeruginosa* activities of colistin sulfate U.S.P. fractions with their analytical HPLC elution profile.

FIG. 9 are analytical HPLC profiles of five separate colistin lots.

FIG. 10 illustrates changes in the pH of colimycin solutions over time and the pH stability of a colistin component IV solution.

FIG. 11 are graphs of HPLC profiles of colimycin dissolved in ammonium sulfate at pH 2.0 analyzed after incubation at room temperature for 45 minutes, 2 hours, 3 hours and 4 hours.

FIG. 12 is an analytical HPLC profile of fractionated colistin component IV collected by preparative HPLC.

FIG. 13 is an analytical HPLC profile of colistin component IV phosphate prepared by exchanging sulfate ions for phosphate ions and desalting on a C-18 reverse phase resin.

FIG. 14 shows a gravimetric titration of colistin component IV free base.

FIG. 15 shows a comparison of the bactericidal activity of colistin component IV hydrochloride and colimycin preparation against *Pseudomonas aeruginosa.*

FIG. 16 compares titration of colistin component IV sulfate and colistin component IV hydrochloride with NaOH.

FIG. 17 illustrates the stability of colistin component IV sulfate solutions after incubation for 19 days at various temperatures.

FIG. 18 are graphs comparing aerosolization times required for aerosolization of 4.0 ml solutions of saline, colistin component IV sulfate and colimycin.

DETAILED DESCRIPTION OF THE INVENTION

The current invention concerns a discovery that a substantially pure colistin, its isolated and separated components, their mixture or their pharmaceutically acceptable salts have a high potency against bacterial pulmonary infections caused by *Pseudomonas aeruginosa* when administered by aerosolization or as a dry powder in a formulation of the invention. Such potency is several fold higher than that of the currently used colistin prodrug colimycin.

The invention utilizes the substantially pure colistin, its components or salts individually or in admixture to provide a colistin aerosol formulation or dry powder formulation for efficacious delivery of the nebulized colistin into the endobronchial space by jet or ultrasonic nebulizers or by dry powder or metered dose inhalers. The formulation comprises 1–50 mg/ml, preferably about 2–20 mg/ml in an aqueous solution, preferably saline, ranging from a full (0.9%) to a half strength, so that the formulation is preferably always isotonic. The formulation is delivered in 2–5 ml volumes twice daily.

The aerosol formulation is easily nebulized into colistin aerosol having particle sizes between 1 and 5μ. necessary for efficacious delivery of colistin into the endobronchial space for treatment and prevention of pulmonary *Pseudomonas aeruginosa* or other susceptible bacterial infections such as *Stenotrophomonas maltophilia* infections. The aerosol formulation is temperature stable in predissolved sterile solution, has a physiologically acceptable pH of 4–7.5, preferably 6.5–7.0, and over a five year long shelf-life.

The invention also utilizes the substantially pure colistin, its components or salts individually or in admixture to provide a colistin dry powder formulation for efficacious delivery of the finely milled colistin into the endobronchial space using dry powder or metered dose inhalers. The colistin potency, determined on a mass basis, allows the inhalation of colistin powder, as an alternative therapy to the aerosol. Dry powder inhalation and metered dose inhalation are most practical when administered doses are less than 10 mg.

The invention provides a sufficiently potent formulation of pure colistin, colistin component, a mixture thereof or a pharmaceutically acceptable salt that dry powder or metered dose inhalation of drug particles milled to particle sizes predominantly within a range of 1 to 5 microns is possible and even preferable, particularly for ambulatory inhalation. Such a formulation is convenient because it does not require any further handling such as diluting the dry powder. Further it utilizes the devices that are sufficiently small, fully portable and do not require, for example, an air compressor which is needed for a jet nebulizer. Additionally, the dry powder formulation has even longer shelf-life than the liquid colistin formulation for aerosolization.

The dry powder formulation comprises 0.5 to 100 mg, preferably about 1 to 10 mg, of powder in an amorphous or crystalline state in particle sizes between 1 and 5 microns in mass median average diameter necessary for efficacious delivery of colistin into the endobronchial space for treatment and prevention of *Pseudomonas aeruginosa* or other susceptible bacterial infections such as *Stenotrophomonas maltophilia*. The dry powder formulation is delivered 1 to 4 times daily, preferably twice daily. The dry powder formulation is temperature stable and has a physiologically acceptable pH of 4.0–7.5, preferably 6.5 to 7.0, and an over five year long shelf life.

I. Pure Biologically Active Colistin and Components Thereof

The anti-*Pseudomonas aeruginosa* active compound of the invention is a substantially pure colistin, isolated as individual colistin components, their mixtures and their respective pharmaceutically acceptable salts.

A. Identification and Characterization of Active Compounds

The active compound of the liquid or dry powder formulation of the invention for treatment and prevention of *P. aeruginosa* or other susceptible bacterial pulmonary infections is colistin, a chemical entity isolated from a fermentation product of *Bacillus polymyxa*, or its isolated purified components.

The active compounds of the invention were separated, isolated, identified and quantitated by fractionation, purification, determination of their UV absorbance, and by their absorbance profiles, absorbance spectrum, amino acid composition, mass spectra, optical polarization and $^3C$ nuclear magnetic resonance spectra.

Colistin, as a free base has a general formula seen in FIG. 1B, wherein the substituent R is used to distinguish main colistin components I, II, III, IV, and other minor components. The $R_1$ substituent of colistin component I is 6-methylheptanoyl, the $R_2$ substituent is isobutyl. The $R_1$ substituent of colistin component III is 6-methyl octanoyl, the $R_2$ substituent is sec-butyl. The $R_1$ substituent of colistin component IV is 6-methyloctanoyl, the $R_2$ substituent is isopropyl. Chemical structures of colistin components I, III and IV are seen in FIG. 1.

The biologically active colistin of the invention thus comprises several chemical entities which, for the purposes of this invention, are identified as colistin I, colistin II, colistin III, colistin IV, or colistin component I, II, III, IV, and other minor components etc. All these entities have the same biological activity on a molar basis against *P. aeruginosa*. Their respective amounts isolated from *Bacillus polymyxa* are not the same. Every single colistin entity whether already identified and characterized, as well as any mixture thereof, and any and all their pharmaceutically acceptable salts and bases are intended to be within the scope of this invention.

The number of individual components in colistin U.S.P. was determined by analytical HPLC as described in Example 1. A typical elution profile for analytical HPLC of colistin sulfate U.S.P. is seen in FIG. 2.

For analytical HPLC, colistin sulfate U.S.P. was dissolved at 10 mg/ml in deionized water. Ten microliters containing 100 micrograms of colistin were injected into a 4.6 mm diameter×150 mm length analytical C-18 reverse phase high performance liquid chromatograph (HPLC) column and eluted at 2.0 ml/min in 23% acetonitrile and 77% ammonium sulfate, pH 2.0. Elution was monitored by absorbance at 220 nm by UV detector. A typical elution profile is seen in FIG. 2.

As seen in FIG. 2, at least 10 independent components are observed under these conditions, with 4 components (labeled I–IV) accounting for greater than 90% of the material absorbing at 220 nm. Under the conditions described, component I elutes at about 2.2 minutes, component II at 2.5 minutes, component III at 3.4 minutes, and component IV at 4.0–4.5 minutes. The respective absorbance at 220 nm was approximately 0.70, 0.20, 0.25, and 1.2 for components I, II, III, and IV.

Figure 3:
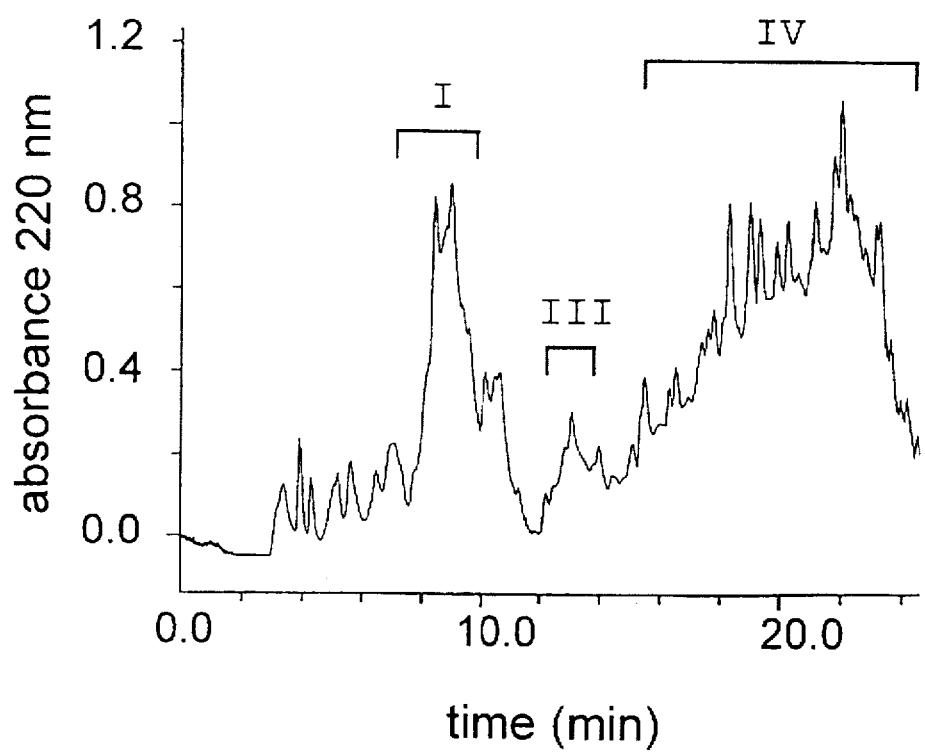
Figure 4:
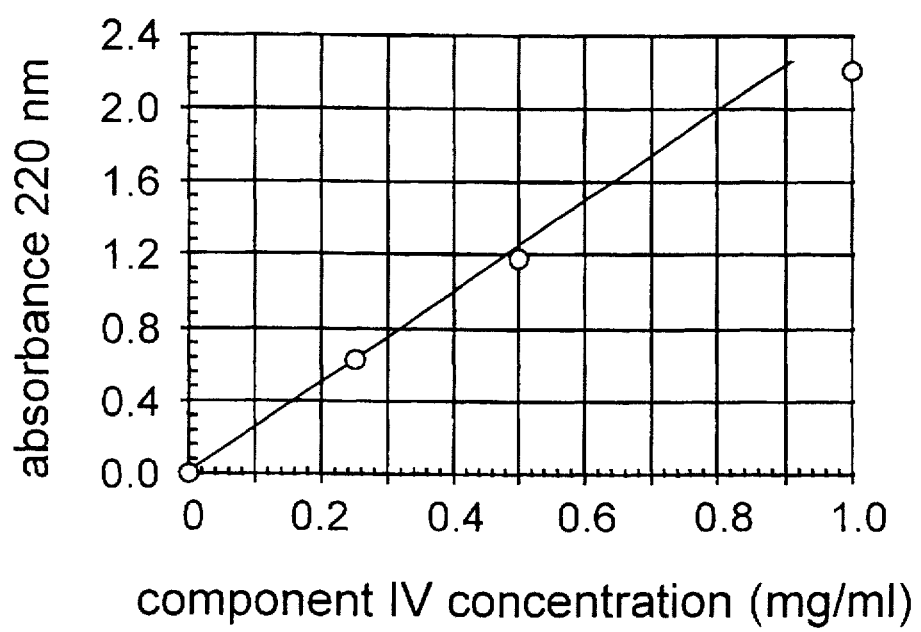

The three most prominent components of colistin sulfate U.S.P. components I, III, and IV of FIG. 2, were fractionated to homogeneity and characterized chemically. The preparative HPLC fractionation technique used is described in detail in Example 2. 300 mg of colistin sulfate was dissolved in 1.0 ml deionized water and injected onto a preparative C-18 reverse phase HPLC column and eluted at 20 ml/min in 23% acetonitrile and 77% ammonium sulfate, pH 2.0. Elution was monitored by absorbance at 220 nm by UV detector. A typical elution profile for preparative fractionation is shown in FIG. 3. Fractionated solutions of components I (100 ml), III, (50 ml), and IV (300 ml) were reduced to dryness by rotoevaporation and components were extracted from inorganic salts by dissolution in 50 ml pure methanol. The relative amounts of each component isolated were determined by assuming that each entity had a similar extinction coefficient at 220 nm. Sufficient material was isolated from component IV for an accurate extinction coefficient to be determined, as shown in FIG. 4. As seen in FIG. 4, dissolution of 1.0 mg of dry component IV sulfate salt into 1.0 ml water yielded an absorbance of 2.25 at 220 nm. When diluted with one volume of deionized water to 0.5 mg/ml, the solution had an optical density of 1.20. Further dilution 0.25 mg/ml yielded a solution of component IV sulfate with optical density of 0.63. Linearity of optical density at 220 nm observed between 0.5 mg/ml component IV and 0.25 mg/ml component IV, as seen in FIG. 4, demonstrates that absorbance readings below about 1.0 are within the linear range and are appropriate for determining component concentrations.

Figure 5A:
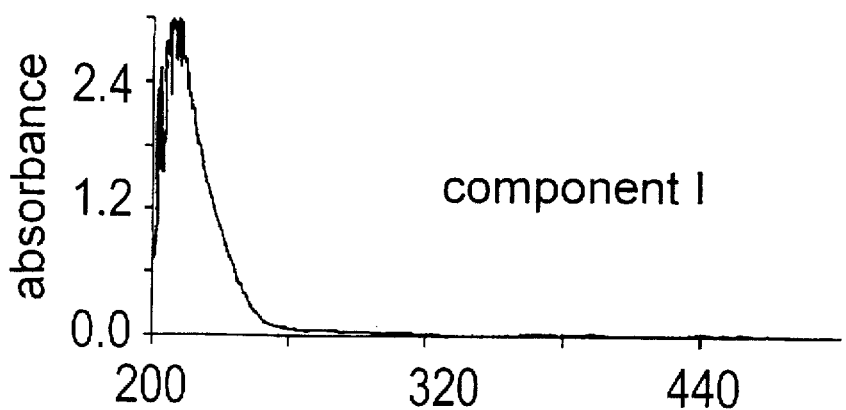
Figure 5B:
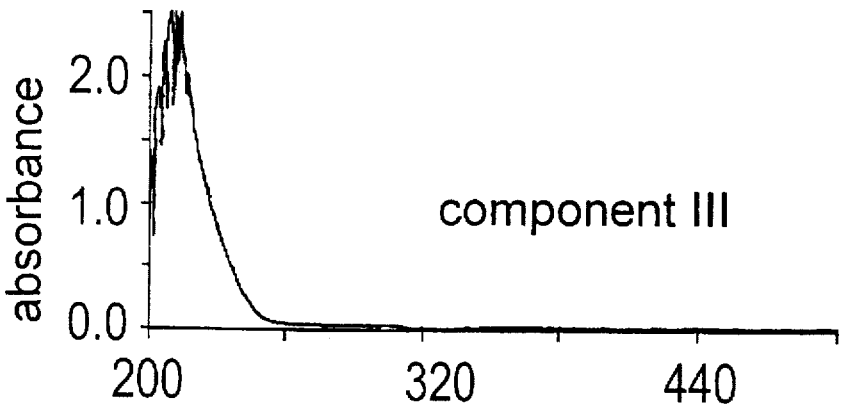
Figure 5C:
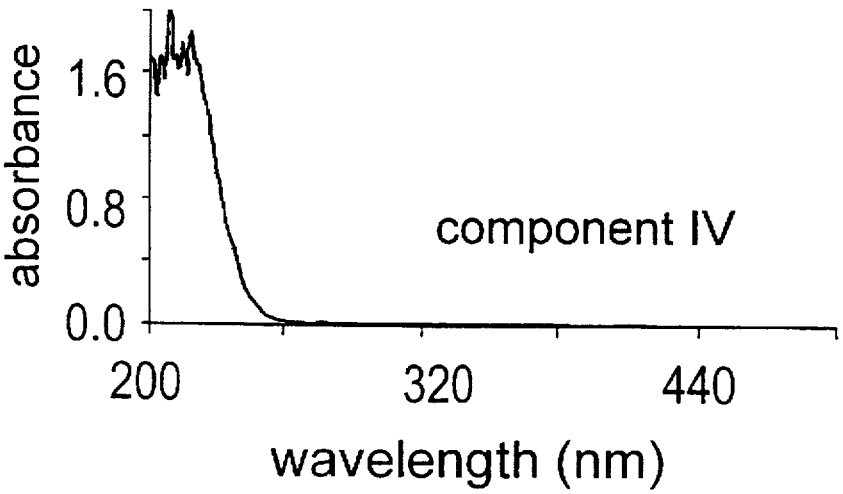

The UV absorbance spectra, at a concentration of 1 mg/ml for component I, III and IV are shown in FIG. 5.

As seen in FIG. 5, colistin components I, III and IV have a very similar absorbance spectrum at wavelength between 200–250 nm. Variation in relative absorbance signals is attributed to the respective quantities of material analyzed.

In addition to the determination of relative amounts of each component, amino acid analysis of these components and their relative amounts was performed on component I, III and IV following 20 hours hydrolysis. Amino acid analysis was performed by post-column derivatization with ninhydrin using a Beckman System 6300 Amino Acid Analyzer updated to 7300 and coupled with a System Gold softwater system. The method is a modification of the method described in Anal. Chem., 30:1190 (1958)as adapted to single column analysis according to Anal. Chem., 35:2055 (1963).

The general procedure for the 16 common amino acids involves weighing a sample into a clean tube, adding an internal standard (generally norleucine), adding 6N HCl, phenol, and a thiol, evacuating the tube, and hydrolyzing for 20 hours at 115° C. Samples of cysteine+cystine analysis are oxidized according to Methods in Enzymology, XI:58 (1967), at 50° C. for 15 minutes with performic acid prior to hydrolysis according to J. Biol. Chem., 247:2828 (1972). Samples for tryptophan are hydrolized in 4.2N NaOH, at 135° C. for 48 hours before neutralization and analysis.

Using this method, components I and IV were found to contain the amino acids diaminobutyric acid, leucine, and threonine at approximately a 3:1:1 ratio. In contrast, component III was found to contain isoleucine in addition to leucine, threonine, and diaminobutyric acid.

Figure 6A:
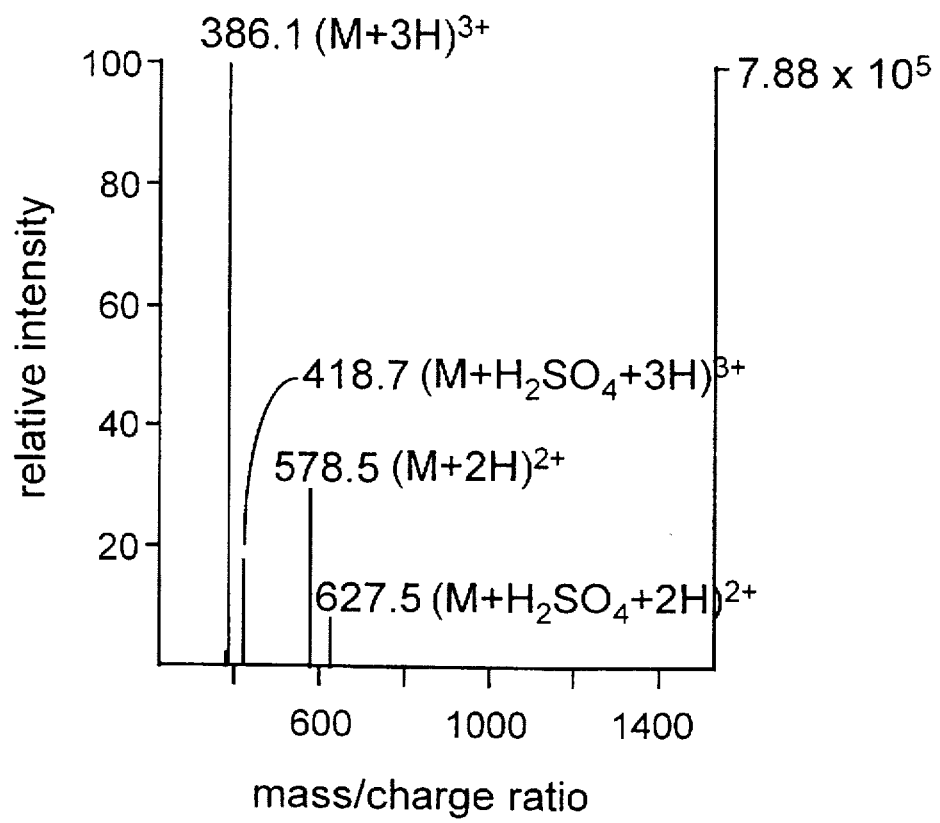

Ion-spray mass spectroscopy of colistin components I, III and IV seen in FIG. 6, demonstrated prominent molecular species mass to charge ratio in the 380–600 range. In colistin component I, seen in FIG. 6A, prominent molecular species of masses of 386.1 and 578.7 amu corresponding to a triply-protonated and doubly-protonated form of a species of 1155 amu, correlating to molecular formula of $C_{52}H_{98}N_{16}O_3$ were observed. In addition, smaller levels of triply protonated sulfate adduct (418.7 amu), and a doubly-protonated sulfate adduct (627.5 amu), were also observed.

Figure 6B:
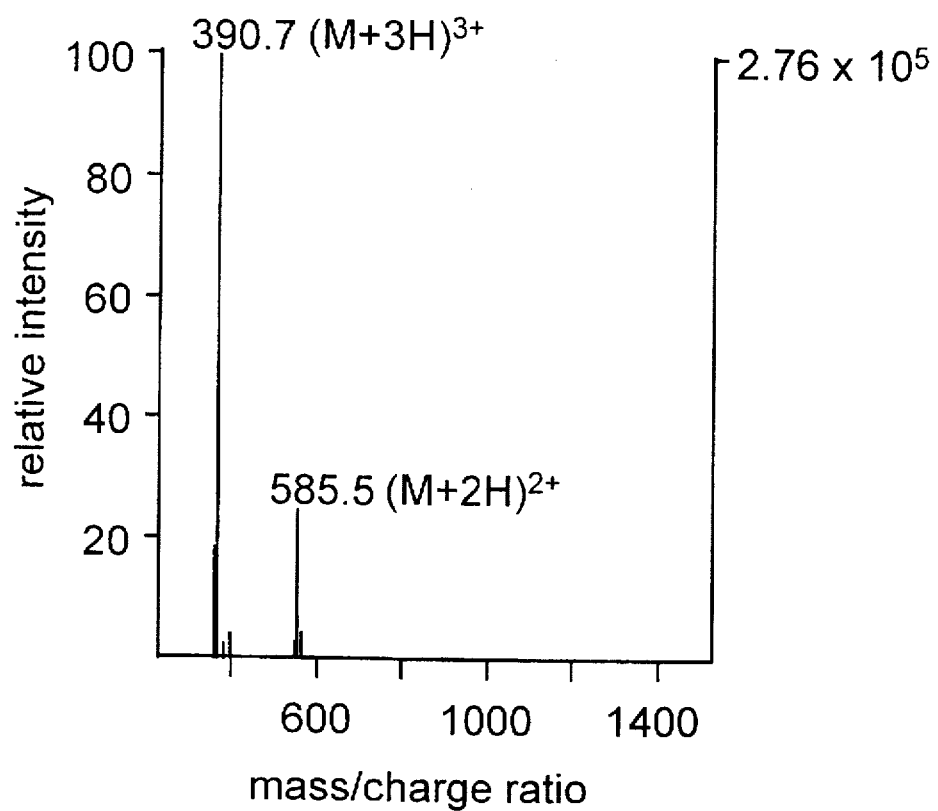

Ion-spray mass spectroscopy of colistin component III, seen in FIG. 6B, demonstrated prominent molecular species of masses of 390.7 amu and 585.5 amu, corresponding to a triply-protonated and doubly-protonated form of a species of 1169 amu, correlating to molecular formula of $C_{53}H_{100}N_{16}O_{13}$.

Figure 6C:
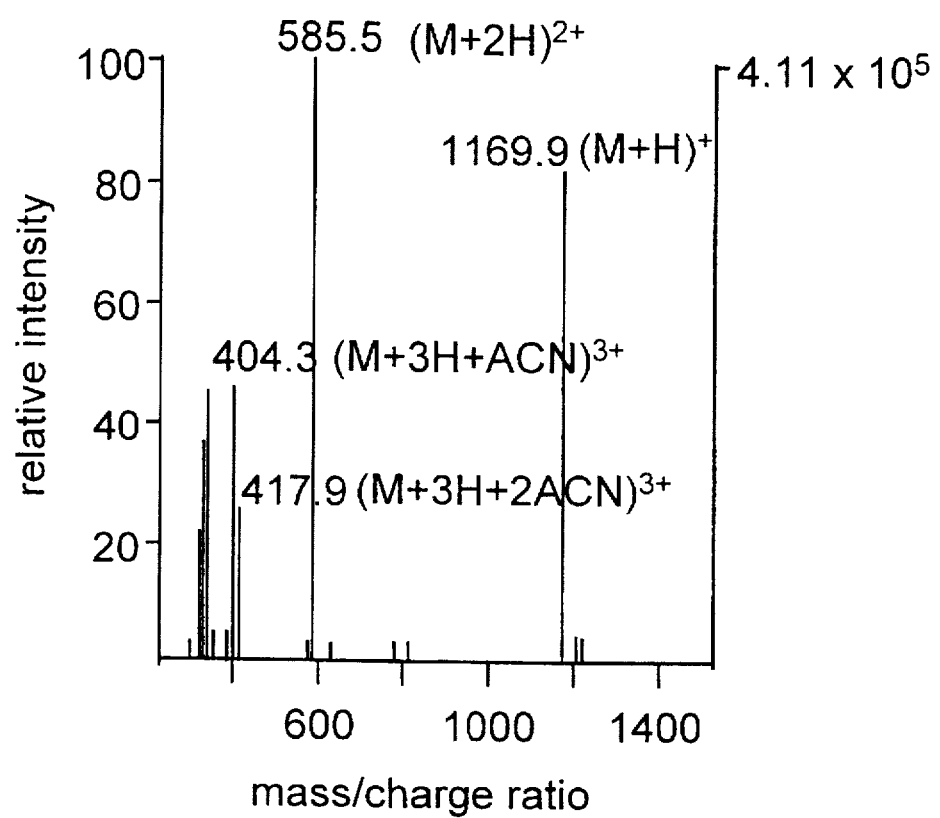

Ion-spray mass spectrometry of colistin component IV sulfate, seen in FIG. 6C, demonstrated prominent species at 585.5 and 1169.9 amu, corresponding to a doubly protonated and singly-protonated form of a species of 1169 amu, correlating to a molecular formula of $C_53H_{100}N_{16}O_{13}$ (identical to that component III). In addition, less abundant species of 404.3 and 417.9 amu represent a triply-protonated species of 1169 amu, and the same entity with a single acetonitrile adduct, respectively.

Spectra and designations for components I, III and IV are shown in FIGS. 6A–6C.

Additional identification of the isolated colistin components was performed by optical polarimetry. For this purpose, dried fractions of components I–III were suspended in sterile irrigation water at concentrations of about 5 mg/ml. The abilities of component I–III solutions to rotate plane-polarized light from the sodium D line (589 nm wavelength) were determined using a Perkin-Elmer 241 polarimeter and a 1 dcm cuvette. The measurements were performed at 25° C. Normalized rotations, obtained by dividing observed rotations by compound concentrations expressed in grams/mL, were then determined. The following values were obtained. The colistin component I is a levorotary compound which rotates to −47°; colistin component III is a levorotary compound but rotates to −42°; colistin component IV is also levorotary but rotates only to −46°.

Further identification of individual colistin components was achieved by $^{13}C$ nuclear magnetic resonance (NMR) spectroscopy. Nuclear magnetic resonance for each of the three components was determined with dried fractions of component I, III or IV suspended in 0.5 mL volumes of $D_2O$ (99.9% D, Cambridge Isotope Laboratories, Woburn, Mass.) for $^{13}C$ spectroscopy. Sodium3-(trimethylsilyl)-propionate-2,2,3,3-d4 was used as an internal standard. At least 200,000 acquisitions for each compound were made on a NMR spectrometer with a data processor at an observed frequency for $^{13}C$ of 75.5 MHz, a tip angle of 29.66 degrees, a recycle time of 181 msec, and a spectrum width of 10000 Hz. Representative $^{13}C$-NMR spectra for components I, III and IV are shown in FIG. 7. Component I can be discriminated from the other two species by the absence of carbons with chemical shifts between 0 and 20 ppm, while component III shows three such carbons (13.1 ppm, 13.4 ppm, and 18.1 ppm) and component IV has a single carbon with chemical shift between 0 and 20 ppm (13.2 ppm).

13Carbon NMR spectra (ppm in $D_2O$) have the following values:

Colistin I $^{13}C$ NMR (ppm in $D_2O$): 175.81, 175.65, 175.54, 175.08, 174.97, 174.30, 69.88, 69.31, 68.97, 62.57, 62.54, 61.93, 56.09, 55.96, 55.93, 55.01, 54.97, 54.66, 54.61, 54.56, 54.53, 54.49, 54.36, 54.21, 54.17, 54.06, 53.78, 53.65, 39.59, 39.48, 39.40, 39.33, 39.31, 38.38, 31.54, 31.51, 31.47, 31.40, 31.20, 31.08, 29.92, 28.92, 28.27, 27.38, 27.32, 27.26, 25.17, 24.73, 24.68, 23.98, 23.24, 23.18, 22.04, 21.67.

Colistin III $^{13}C$ NMR (ppm in $D_2O$): 177.64, 177.30, 177.19, 175.76, 175.60, 175.25, 175.04, 174.99, 174.81, 174.65, 174.27, 69.87, 69.49, 62.60, 61.92, 55.79, 54.91, 54.64, 54.59, 54.37, 54.19, 54.07, 53.86, 53.82, 39.63, 39.43, 39.32, 38.38, 38.22, 36.41, 31.65, 31.48, 28.67, 28.33, 27.32, 27.25, 25.13, 24.75, 24.68, 23.97, 23.78, 22.04, 21.98, 21.65, 21.44, 18.11, 13.40, 13.06.

Colistin IV $^{13}C$ NMR (ppm in $D_2O$): 180.33, 177.66, 177.32, 176.07, 175.73, 175.58, 175.51, 175.04, 174.93, 174.58, 174.23, 69.78, 69.15, 62.41, 61.78, 55.97, 55.8, 54.78, 54.55, 54.4, 54.03, 53.91, 53.58, 42.48, 41.81, 39.42, 39.23, 39.14, 38.82, 38.26, 38.11, 36.3, 33.33, 32.46, 31.58, 31.46, 31.4, 31.07, 31.03, 28.54, 28.28, 27.19, 27.14, 25.11, 24.55, 23.83, 22.99, 21.94, 21.55, 21.34, 13.36.

Components I, III and IV were tested for their anti-*Pseudomonas aeruginosa* activity.

B. Biological Activity of Colistin and Colistin Components

The relative anti-Pseudomonal activities of fractionated colistin components were determined by collecting 0.4 ml fractions (0.2 minute increments) of an analytical HPLC run such as the one shown in FIG. 2 from 1.0 minutes through 5.0 minutes. The experiments were performed as outlined in Example 3.

Briefly, HPLC fractions were dried by vacuum centrifugation, suspended in 400 microliters of bacterial growth medium, filter sterilized through a 0.45 micron cellulose acetate membrane, and then a series of 2-fold dilutions were used to assess the relative anti-Pseudomonal activities in a microtiter cell turbidity assay against *Pseudomonas aeruginosa* strain 27853.

Figure 8:
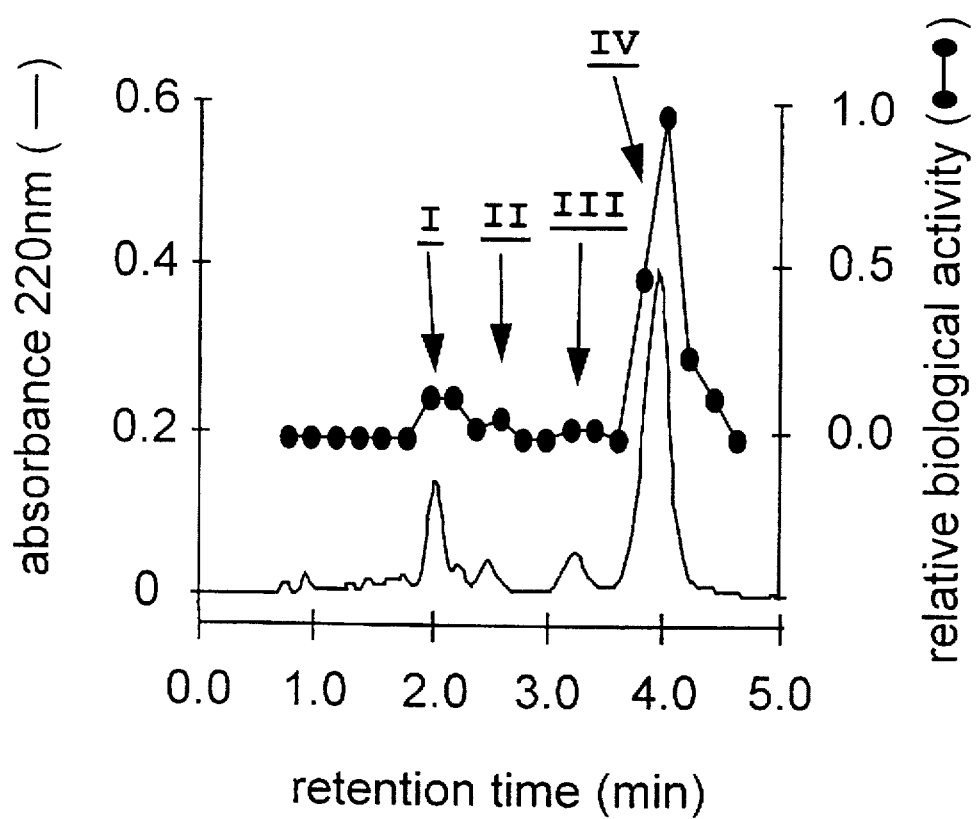

Results are seen in FIG. 8 which shows absorbance at 220 nm of individual colistin components and their relative anti-Pseudomonas activity superimposed over the elution profile. FIG. 8 shows a plot of the relative anti-Pseudomonal activity for each fraction collected (normalized such that the most active fraction is given a value of 1.0 and inactive fractions are given a value of 0.0) and compares it to the HPLC elution profile monitored at 220 nm by UV detector.

FIG. 8 demonstrates that each major colistin component (I–IV) shows biological activity which is proportional to the area of its UV absorbance, and thus that any individual colistin component would have comparable therapeutic effect in treating *Pseudomonas aeruginosa* infections.

Identified and characterized colistin components were further investigated for reproducibility of recovery of these components from a commercially available source.

The above results show that colistin sulfate exists as a mixture of several components having different chemical and physical properties, which components may be separated, isolated and purified.

In order to determine whether the commercially available non-sterile oral colistin sulfate powder of different lots provides consistently the same spectrum of active components, and in approximately the same relative amounts, five different lots of colistin sulfate powder were investigated. The experimental procedure is described in Example 1. Results are seen in FIG. 9.

Figure 9:
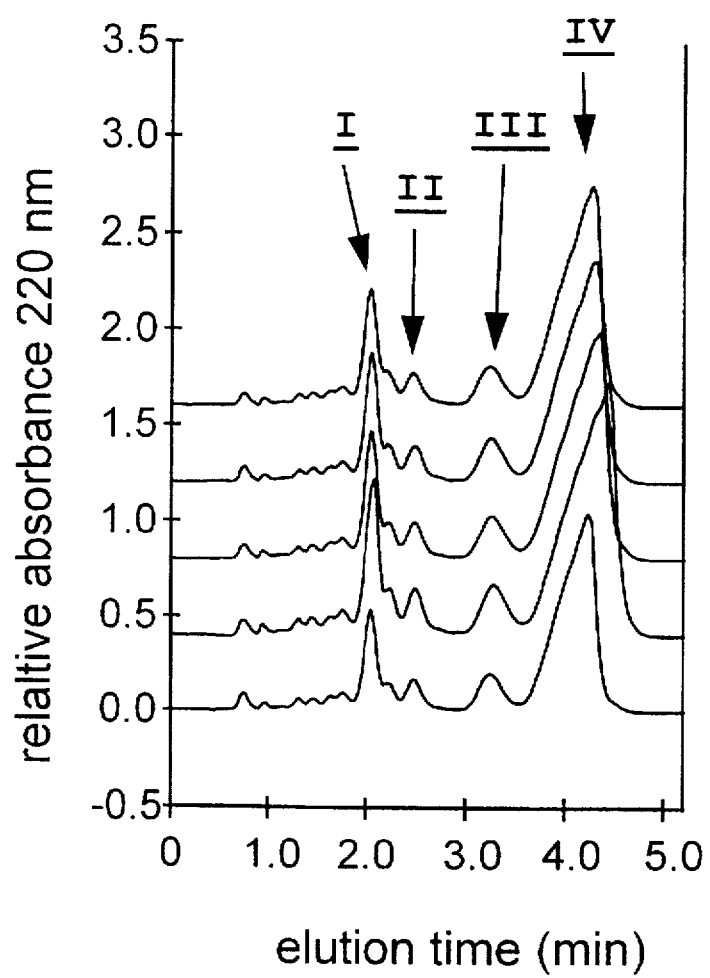

The profiles of five separate lots of colistin sulfate U.S.P. seen in FIG. 9 were found to be almost identical in composition. In all five lots, the major component by weight appears to be colistin component IV, which under these chromatographic conditions, typically eluted between 3.5 and 5.0 minutes. Component I from all five lots eluted from about 1.8 to about 2.3 minutes. Components II and III similarly had consistent elution in all five investigated lots. As seen in FIG. 9, colistin component IV was consistently the major component of colistin sulfate U.S.P. by weight.

These results show that the commercially available colistin sulfate yields consistently the same results and may be used as a source of obtaining purified isolated colistin components of the invention.

II. Comparison of Colistin and Colimycin

The invention is based on finding that a substantially pure colistin, colistin component or a mixture thereof has a high therapeutic potency as an anti-*Pseudomonas aeruginosa* or anti-*Stenotrophomonas maltophilia* agent. The therapeutic potency of aerosolized purified colistin is several fold higher than the potency of the currently used colistin prodrug colimycin administered in the aerosol formulation. Colimycin aerosol has several severe flaws making its aerosolized treatment unpredictable and uncontrollable.

A. Colistin and Colimycin Aerosol Formulation

Colimycin is commercially available from Parke-Davis as Coly-Mycin M Parenteral, a sterile dry powder formulated for intravenous or intramuscular injection in 500,000 and 1,000,000 unit dosages. A typical dose for aerosolization is 2,000,000 units every 8 hours three times a day, or 6,000,000 units per day. That represents about 150 mg of colimycin/8 hours or 450 mg of colimycin/day dosage. For aerosolization, this amount of colimycin must be dissolved and aerosolized.

Colistin of the invention is a substantially pure colistin or colistin component which is a purified fermentation product of *Bacillus polymyxa*. Colistin of the invention has several times higher comparable anti-*Pseudomonas aeruginosa* activity to the colimycin with total administered daily amount of about 2–250 mg.

B. Disadvantages of Colimycin Aerosol Formulation

Colimycin, as already discussed above, is only a prodrug of colistin and by itself is inactive against *Pseudomonas aeruginosa*. It must, therefore, be first converted by hydrolysis into the active compound colistin. Such conversion occurs slowly in situ in the recipient patient body with about only 3% of the drug being converted in an hour. Due to this in situ conversion, the rate of the conversion is unpredictable and unmeasurable and therefore the actual therapeutic potency of the colimycin cannot be determined. Moreover, the potency of the colimycin solution varies after reconstitution depending on a variety of extraneous conditions such as the length of time of colimycin dissolution in the solvent, the solution pH, temperature, etc. Its potency, therefore, cannot be readily verified making the accurate calculation of delivered dose very difficult if not impossible. Furthermore, when colimycin is dissolved in aqueous solution prior or during the delivery, various impurities and degradation by-products, such as formaldehyde, a known toxin and carcinogen, and sulfites, known bronchoconstriction agents, are produced and released. These by-products cause the above discussed secondary undesirable symptoms.

Additionally, because the conversion rate from colimycin to colistin is unknown and undeterminable and because colimycin contains substantial amount of impurities, much larger amounts of colimycin must be aerosolized in order to achieve an additional therapeutic effect. This leads to an additional disadvantage of using colimycin for aerosolization, because concentrations of colimycin above about 20 mg/ml are prone to foaming when nebulized, resulting in inconsistent delivery of drug to the patient. In order to reduce the incidence of foaming, more dilute solutions are required, which result in a much longer aerosolization time, a significant inconvenience to the patient. Moreover, when parenteral colimycin is dissolved for aerosolization, its pH promptly begins to rise to nonphysiological levels of above 7.5. Solutions having pH above physiological pH are not well tolerated by the respiratory system, and can result in significant patient discomfort.

For the above reasons, the currently available aerosol or dry powder formulations of prodrug colimycin have severe limitations which makes it inconvenient, unpredictable and even hazardous to a patient. The significantly higher doses of colimycin required for effective treatment of *Pseudomonas aeruginosa* or other susceptible bacterial infections relative to purified colistin, one of its components, and admixture thereof, or a pharmaceutically acceptable salt thereof make it less advantageous for formulation in a dry powder for delivery by dry powder inhaler or metered dose inhaler. This is because the current maximum payload of such devices is 10 to 20 mg of material. In addition, the unpredictable hydrolysis rates and non-physiological pH of hydrated colimycin make its administration as an inhaled dry powder potentially dangerous.

1. Impurities and Contaminants Present in Colimycin

In order to determine the actual proportion of colistin base to total mass in colimycin, the presence of impurities and contaminants in commercially available colimycin was investigated.

This study was based on the following assumptions and calculations. First, a standard dosage of colimycin (Coly-Mycin M Parenteral) contains 150 mg colistin base equivalent. For calculation purposes, if all this activity was present as a prodrug form of component IV, the prodrug would have a molecular weight of 1749.8 g/mol ($C_{53}H_{100}N_{16}Na_5O28S_5$) while colistin component IV base ($C_{53}H_{100}ON_{16}O_{13}$) has a molecular weight of 1169.4 g/mol. Therefore, a rough estimate of the calculated weight of prodrug corresponding to 150 mg of colistin base equivalent of colimycin is approximately 224.4 grams, i.e. 150×[1749.8/1169.4]. To determine the actual mass of material present in the standard dosage of colimycin formulation, a study was performed to determine the average actual weight per vial of the commercially available colimycin according to Example 10.

The average mass contained in the studied vials was determined to be 402.3 mg, representing an average excess in mass of 177.9 mg over the theoretical dosage of 224.4 grams. Therefore, in average each vial contained about 44% of impurities and only about 56% of the active colistin. Any aerosolized dosage of colimycin is, therefore, only ~60% drug and the aerosolized amount has to account for this dilution.

Colistin of the invention is a substantially pure biologically active colistin or colistin component which does not need to be converted to the active drug and does not contain any substantial amount of impurities or contaminants which dilute its activity. Consequently its potency is standard and constant and the dosage from 1–50 mg/ml delivered in 2–5 ml, found to be effective in treating *Pseudomonas aeruginosa*, delivered by the aerosol to the lungs, is at least about two times smaller than the amount of colimycin. Furthermore, with the decreased amount of dissolved solids and increased potency, the amount of active compound is even smaller. This directly leads to less surfactant activity resulting in less or no foaming during aerosolization.

2. Foaming During Aerolization

Another disadvantage of the colimycin aerosol formulation is its extensive foaming during aerosolization caused by significant quantities of unidentified materials contained in colimycin. A typical 150 mg dose of dry powder for injection has an actual mass of over 400 mg. When this material is dissolved at colistin-equivalent concentrations above about 20 mg/ml, the solution is prone to significant foaming and sputtering in the jet nebulizer which reduces the amount of aerosolized drug.

3. PH Instability of Colimycin Solution

Another problem connected with the colimycin solution is its pH instability. Basic solutions are poorly buffered by the human pulmonary system, and therefore are not well tolerated as aerosols. It is, therefore, important that the pH of the aerosol solution is stable and within the physiologically acceptable levels.

Acidic stability of the colimycin solution was determined according to Example 11. Briefly, colimycin (405 mg) was freshly dissolved in water to achieve 10.0 mg/ml, 15.0 mg/ml, and 20.0 mg/ml solutions. These values correspond to concentrations of 3.7 mg/ml, 5.6 mg/ml and 7.4 mg/ml colistin base equivalent. Solution pH was monitored continuously at various times from 1 minute to 180 minutes and pH values and times were recorded.

In all cases, the pH of the colimycin solution increased rapidly from the starting pH of 6.80 to levels exceeding pH 7.5 within 3 minutes, and continued to rise over 2 hours to physiologically unacceptable levels between 7.70 and 8.00. Results are seen in FIG. 10.

Purified colistin of the invention has a stable and safe range of pH between 5.5 and 7.5, with the most optimal pH around 6.5. The pH values of the purified colistin in solution are easily adjustable and when adjusted, they are stable, as shown in FIG. 10. Colistin in solution, premixed and stored for long periods of time is stable and does not rise as observed in case of colimycin.

4. Formaldehyde/Sulfite Content of Colimycin Solutions

Formaldehyde is a general respiratory irritant and a suspected carcinogen. Sulfite is a known bronchial irritant causing bronchospasm and chest tightness. The presence of these compounds in the solution for aerosolization or their production during aerosolization is therefore highly undesirable.

Colimycin is a sodium sulfomethyl derivative of a prodrug of colistin in which colistin base is conjugated with up to 5 moles of formaldehyde and 5 moles of sodium sulfite (*British J. Pharmacol.*, 23: 552–574 (1964)). Colimycins are designed to hydrolyze in water to release biologically active colistin base. For each molecule of colistin base released, up to 5 molecules of formaldehyde and 5 molecules of sulfite are released simultaneously.

The purified colistins of the invention are not derivatized and thus do not contain sulfites and formaldehyde. Their aerosol formulation does not cause bronchospasm or other pulmonary irritations.

5. Complexity of Parenteral Colimycin

The parenteral colimycin is not a single entity but is a complex form which reacts differently to various conditions. This is not desirable for a formulation which needs to have stable and standard activity and stability under different conditions in order to be therapeutically viable and commercially practical and suitable.

The complexity of colimycin in the parenteral form was investigated according to Example 12 by dissolving 150 mg of colistin base equivalent of 402.9 mg of parenteral colimycin in 10 ml of 105 mM ammonium sulfate buffer, pH 2.0. The low pH of this solvent was predicted to rapidly hydrolyze the sulfomethyl conjugate of colimycin.

At various time points after dissolution, aliquots equivalent to 150 µg of colistin base were submitted to reverse phase HPLC. Eluate was monitored by absorbance at 220 nm by UV detector.

Figures 11A, 11B, 11C, 11D:
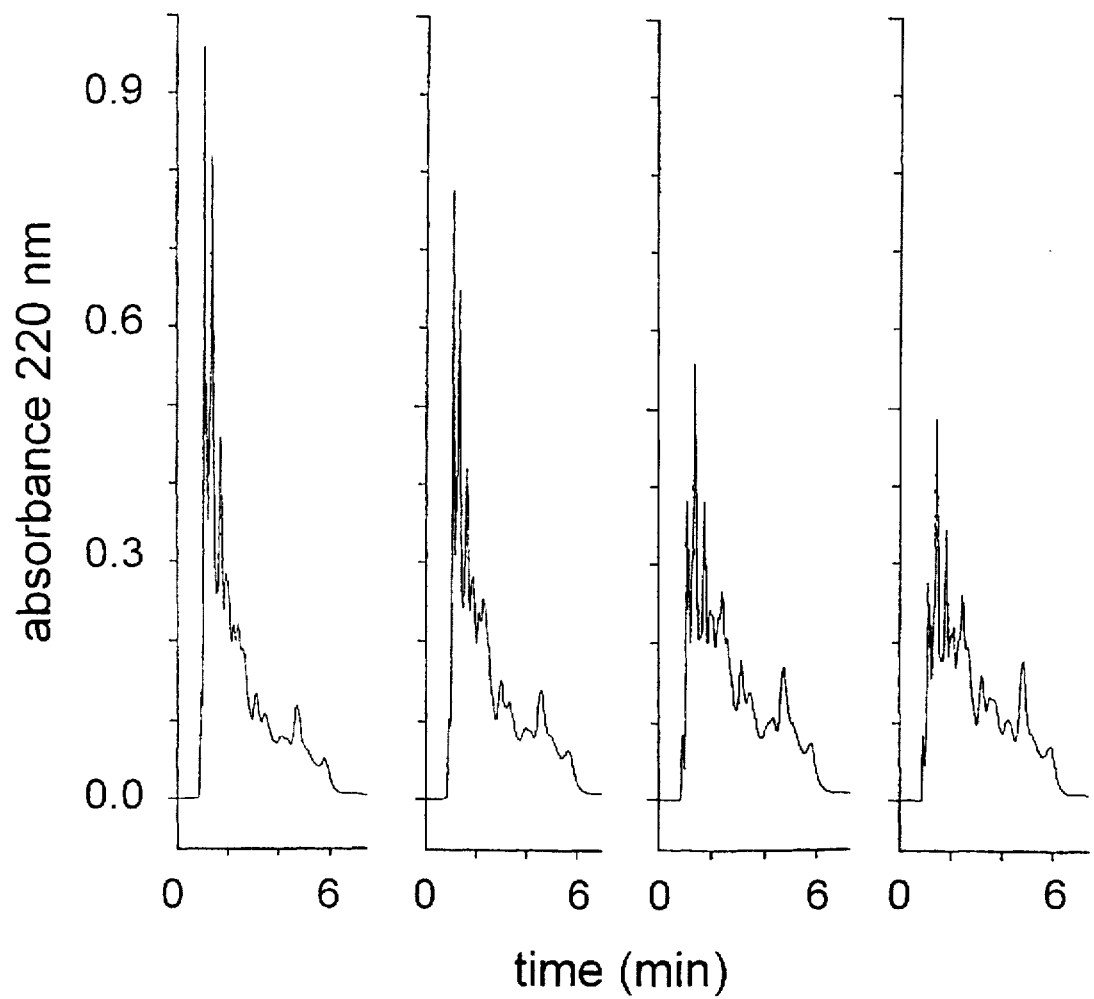

HPLC elution profiles of colimycin seen in FIG. 11 demonstrated the presence of at least 8 distinct species which absorb at 220 nm when 150 micrograms of colistin base equivalents of colimycin were analyzed. As expected, relative quantities of each species, as approximated by peak height seen in FIG. 11, changed during incubation in pH 2.0 buffer. As seen in FIG. 11, the quantity of the individual species decreased with time of incubation at room temperature; panel A shows the HPLC elution profile of colimycin at 45 minutes; panel B shows the HPLC elution profile at 2 hours; panel C shows the HPLC elution profile at 3 hours; and panel D shows the HPLC elution profile at 4 hours. This data demonstrates that the chemical composition of colimycin changes over time.

These results show yet another disadvantage of the colimycin used for aerosol treatment of *Pseudomonas aeruginosa*. In order to accurately characterize the aerosolization of colistin solutions, the stability of colistin formulations for aerosolization, the systemic absorption of aerosolized colistins, and the metabolic profile of absorbed colistins, it is necessary to develop analytical assays for test agent levels in solutions and biological fluids and tissues. The complexity of the colimycin HPLC profiles indicate that characterization of the aerosolization, stability, absorption, and metabolism of this formulation would be difficult if not impossible.

Colistins of the invention, whether in the mixture of components or as the individual isolated components are characterized as such, are stable and therefore their characterization for aerosolization is possible.

C. Purified Colistin for Aerosol Formulation

The most efficacious aerosol formulation contains the smallest possible therapeutically effective amount of drug delivered in the smallest possible volume in the shortest possible time.

In order to provide substantially pure colistin or its components for aerosol formulation, colistin sulfate was fractionated into its individual components and these components were characterized as described above, and purified to greater than 95% purity by preparative HPLC according to Examples 2-4.

The purification of colistin and its individual components was achieved using a reverse-phase preparative column HPLC. Typically, 100 to 300 mg of commercially available colistin sulfate U.S.P. previously dissolved in deionized water was separated at a flow rate of 20 ml/min, and product elution was followed by UV detector set at 220 nm as described in Example 4.

In the first stage, the individual colistin components were isolated by preparative fractionation from colistin sulfate U.S.P. This step is illustrated in FIG. 3 which shows an HPLC profile of preparative fractionation of colistin IV from commercially obtained colistin sulfate U.S.P. In the run shown in FIG. 3, 210 mg of material was fractionated and the eluates, containing components I, III and IV, were collected in separate vessels.

Figure 12:
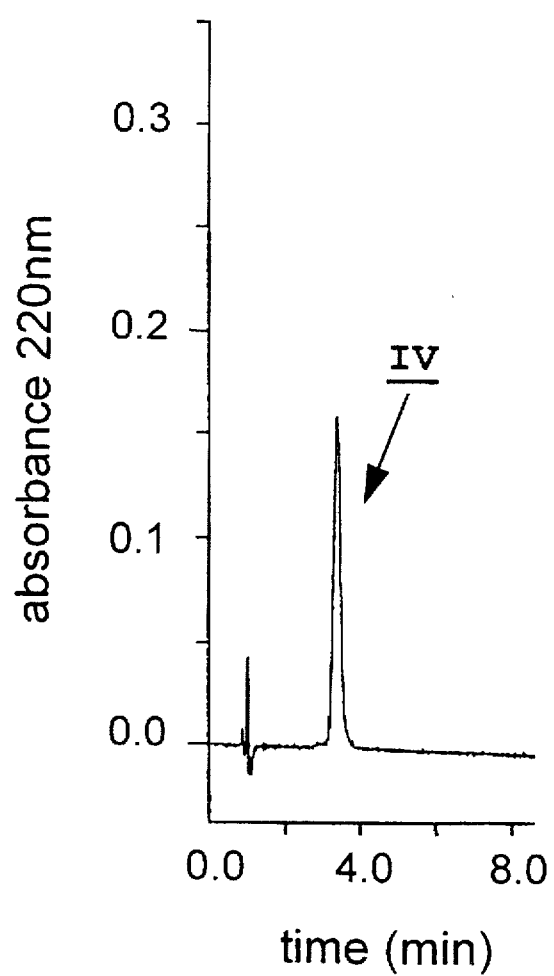

Collected fractions were re-injected again on an analytical reverse-phase HPLC column to verify product purity. FIG. 12 shows an analytical HPLC profile of fractionated colistin component IV collected by preparative HPLC according to FIG. 3. As seen in FIG. 12, only a single entity with a retention time consistent with colistin component IV elution was present.

Other colistin components are purified in the same way until only a single entity is present. The purified colistins are used as an active component in aerosol formulation of the invention.

D. Colistin Pharmaceutically Acceptable Salts

Active purified colistin components used for aerosol formulation are typically prepared as salts which are easy to dissolve and often enhance the biological activity. These salts must be pharmaceutically acceptable.

Unpurified colistin is commercially available as colistin sulfate U.S.P. This colistin is then purified as described above and a pharmaceutically acceptable salt is prepared, preferably as a pharmaceutically acceptable salt selected from those listed in the Definitions. The most preferred salts are sulfates and hydrochlorides.

1. Desalting of Fractionated Colistins

Preparative HPLC fractionation of colistin components results in dilute solutions of single components in mixed acetonitrile/ammonium sulfate solutions. In order to recover purified components from these solutions, the acetonitrile is removed by evaporation, leaving a solution more concentrated in both colistin component and inorganic salt. Inorganic salt can be separated from the colistin component by use of a reverse phase desalting column. Desalting of colistin components is described in Example 5.

Exemplarized by colistin component IV, this component was extracted from the pooled eluates obtained above, by reducing the fraction volume approximately 10 fold with any suitable evaporator. Concentrated component IV containing about 1.0 gram of colistin component IV was loaded onto a chromatography column packed with C-18 reverse phase resin previously washed with 4 void volumes of acetonitrile followed by 4 void volumes of deionized water. Solvents were passed through the column via peristaltic pump running at 1 ml/min and fractions were collected. After loading the colistin component IV onto the column, the resin was washed with 1 void volume of water and eluted with 50 ml of 40% acetonitrile. Fractions were assayed for colistin component IV content by spotting 2 microliter aliquots onto a silica G thin layer chromatography plate which after drying was sprayed with a 0.75% solution of ninhydrin in 100% ethanol, and heated to 100° C. The presence of a purple color which signifies a presence of primary alkyl amines, including colistin was observed. Ninhydrin-positive fractions were pooled, dried, dissolved in water, transferred to a clean, pre-weighed 20 ml glass screwcap vial, frozen on dry ice, and lyophilized to dryness. Other colistin components were treated in the same way.

A typical desalting reaction yielded about 650 mg of dry colistin component IV sulfate per gram (as determined by absorbance at 220 nm) for each 1.0 gram loaded on desalting resin. The absorbance spectra of purified materials were obtained and are seen in FIG. 5.

2. Precipitation of Colistin Free Base

An alternate strategy to desalting purified colistin fractions on C18 resin was precipitation of individual concentrated colistin components by addition of a base, such as, for example, 10N NaOH until the solution pH reached 11.0. Colistin free base was obtained according to Example 6. The precipitate was collected, washed and dried under vacuum for at least 24 hours. Titration of this material using 1.0M HCl suggested that although colistin free base could be obtained by this procedure, it was not uniformly produced, the residual NaOH was not completely removed and the overall yield of this procedure was lower than using desalting, averaging 200 to 300 mg recovery per gram colistin fractionated.

3. Exchange of Colistin Components Salt Counterions

Pharmaceutically acceptable salts of colistin and colistin components are prepared by exchange of colistin salt counterions essentially as described in Example 7.

Generally, purified colistin sulfate or colistin component sulfate is dissolved at a concentration of about 20 g/liter (1 gram per 50 ml) in a solution containing 2M sodium or potassium salt of the desired anion, such as for example 2M $NaH_2PO_4$. The anion exchange proceeds on the following basis. For example colistin component IV sulfate contains 3 moles of sulfate counterions per mole colistin, with a formula weight of 1554 grams/mole. Thus, 20.0 grams of colistin component IV sulfate has $(20\times3/1554)=0.0386$ moles or 38.6 mmoles of sulfate ions which are competing with 2 moles of phosphate ions, creating a greater than 50-fold excess of phosphate ions.

The mixture is then passed over a desalting resin as described above, washing with one column volume of water, and eluted with, for example, 40% acetonitrile/water at a flow rate of, for example, 1 ml/min. Eluted fractions of, for example, 7 mL are collected and assayed for colistin components by ninhydrin reaction. Ninhydrin-positive fractions are pooled, dried, dissolved in water, frozen on dry ice, and lyophilized to dryness. The material recovered by this procedure contains more than 95% of purified colistin salt or colistin component salt.

Figure 13:
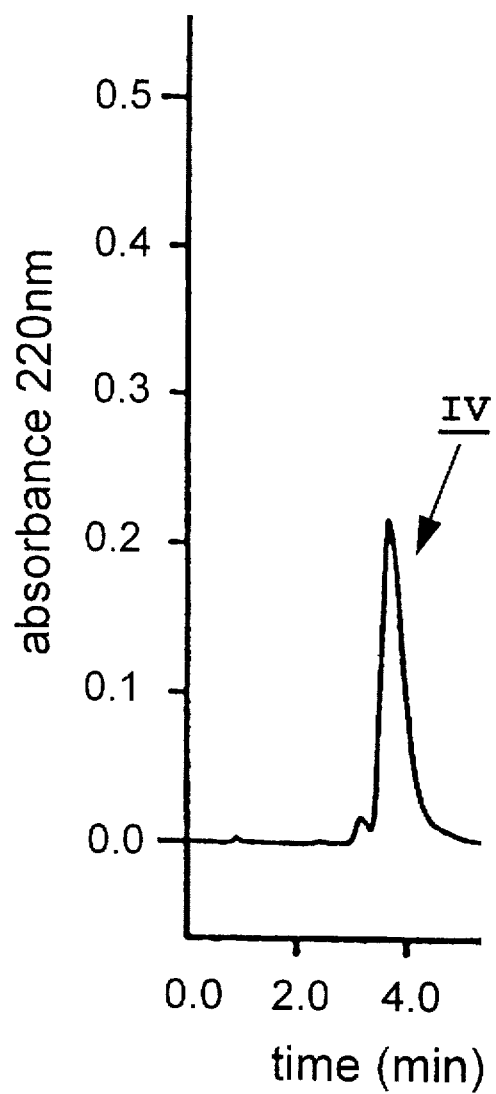

Using the procedure described in Example 7, colistin component IV was treated in this way and the recovered material was found to consist of more than 99% colistin component IV phosphate, with trace levels of colistin component IV sulfate remaining. Analytical HPLC analysis of this material confirmed the presence of colistin component IV. Results are seen in FIG. 13 which shows an analytical HPLC profile of colistin component IV phosphate prepared by exchanging sulfate ions for phosphate ions and desalting on a C-18 reverse phase resin. The retention time of the single entity seen in FIG. 13 is consistent with colistin component IV.

The other salts, for example hydrochloride and citrate, were prepared in the same manner by substituting sodium phosphate monobasic with any other salt such as sodium, potassium, etc., in excess. Calculations as to the amounts of substitute salts are made according to the calculation shown above for sodium phosphate monobasic.

Figure 16:
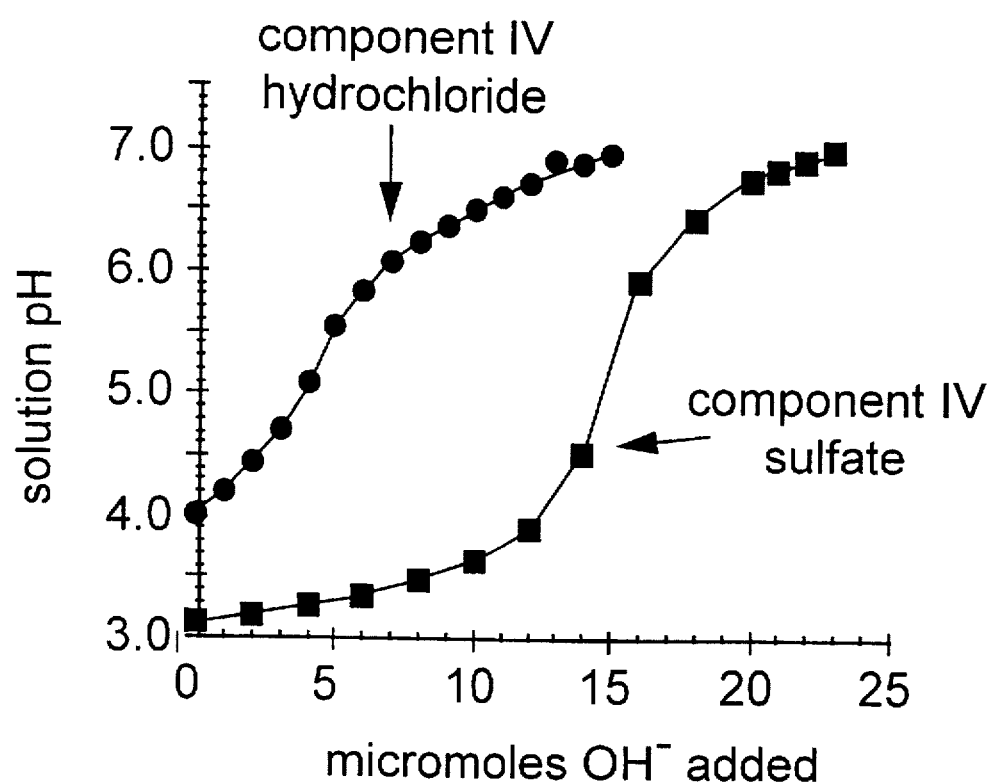

Alternatively, pharmaceutically acceptable salts of colistin and colistin components are prepared by titration of colistin free base or colistin component free base with counterion conjugate acids. Generally, colistin or colistin component free base is suspended in deionized water at a concentration of 10 grams/liter, stirred by magnetic stirrer, and solution pH is monitored by calibrated pH electrode. Dropwise addition of concentrated counterion conjugate acid, for example, 1.21M HCl, is continued until 5 molar equivalents of protons are added, or the pH reaches the equilibration point of 4.5. The solution is then filtered to remove particulates, for example with a 0.45 micron cellulose acetate filter, frozen, and lyophilized until all excess water is removed. This method of titration to generate the pentahydrochloride salt of colistin component IV from component IV free base is shown in FIG. 16 and described in Example 9.

4. Mass Spectral Characterization of Purified Colistin Component IV Sulfate

Mass spectral characterization of sulfate salts of colistin component IV was performed according to Example 8. Results are seen in FIG. 6C.

5. Gravimetric Titration of Purified Colistin

Figure 14:
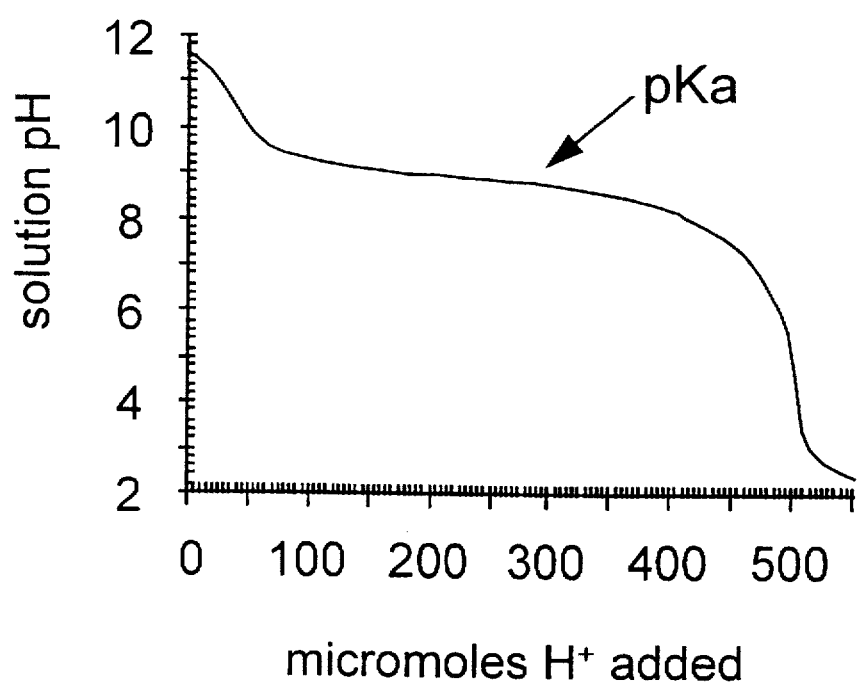

In order to determine the pKa of purified colistin component IV, colistin component IV was submitted to gravimetric titration using the procedure described in Example 9. 107 mg of dry free base was suspended in 10.7 ml of deionized water and 1.21M HCl was added under constant measurement of pH. The starting pH of the suspension was observed to be 11.47, and 2 inflection points were observed during the titration, one at 40 micromoles of HCl added and a pH of 10.2 and a second at 505 micromoles of HCl added and a pH of 4.5. Results are seen in FIG. 14. The first inflection point was inferred to identify neutralization of trace amounts of NaOH remaining in the solid material (40 micromoles×40 micrograms/micromol=1.6 mg or about 1.5% by weight). This was consistent with the solution pH, since 40 micromoles hydroxide ion in 10.7 ml=3.75e-3 molar hydroxide. Since $[H+]\times[OH-]=1e-14$, the proton concentration would be 2.67e-12, and since $pH=-\log[H+]$, $pH=-\log(2.67e-12)=11.57$, fairly close to the observed pH of the colistin A base suspension of 11.47. The second inflection point observed around 550 µMOL of HCl represents the complete protonation of colistin component IV.

These results demonstrate that colistin component IV has a pKa of about 9.0 and therefore is able to provide some buffering capacity at the optimal formulation pH of 6.5.

III. Preparation of Substantially Pure Biologically Active Colistin and A Component Thereof Substantially pure colistin or colistin component free base or salt subject to this invention, namely colistin component I, colistin component II, colistin component III, colistin component IV, etc. (seen in FIG. 1B), are isolated and prepared from non-sterile oral colistin sulfate U.S.P. powder commercially available from Dumex, Ltd., Denmark or from any other source of colistin. The commercial powder is subjected to chromatographic or any other suitable purification.

Typically, the oral colistin powder is dissolved in deionized water or any other suitable solvent at a concentrations ranging from about 0.1 g–300 g/liter. In order to remove particles, the solution is filtered through any suitable filter, preferably through 0.45 micron cellulose acetate filter and, at this point, when required, may be stored at 4° C. for an indefinite period of time.

The above solution is then subjected to fractionation by reverse phase high performance liquid chromatography (HPLC) column, such as, for example, Vydac 218TP C-18 or Beckman Ultrasphere ODS C-18 reverse phase high performance liquid chromatography (HPLC) column, of appropriate length and dimensions, depending on the volume of the solution to be separated. For large scale and volume separation, the separation column is modified and optimized. In alternative, any other separation means able to separate the colistin sulfate into colistin components of the invention can be used. These and any other suitable separation means, equipments and techniques are intended to be within the scope of this invention.

The solution is then eluted with a solvent, such as acetonitrile, propionitrile, succinonitrile, methanol, ethanol, isopropanol and other water miscible organic solvents preferably with about 20–25% acetonitrile in the presence of a running buffer, such as ammonium sulfate, buffer containing preferably about 75–80% of about 50–120, preferably 105 mM ammonium sulfate, at acidic pH, preferably about pH 2.0–3.0. Alternate running buffers include 0.05 to 0.15% trifluoroacetic acid, preferably 0.1%, sodium phosphate, ammonium phosphate, sodium sulfate and acetic acid. The eluate is monitored by absorbance at 220 nm by UV detector, such as for example, Beckman Diodide Array detector module 168.

In order to assure the standard quality of the eluted colistin, each new lot of the oral powder is monitored and its analytical profile is compared to prior colistin batches. Analytical profile of the colistin sulfate is monitored at 220 nm UV for about 5–10 minutes or until the elution is complete.

Elution fractions for each active colistin are then collected, optionally concentrated or dried, stored when required at 4° C., freeze-dried and used for preparation of the liquid or dry powder formulation, as described below.

IV. Antibacterial Activity of Pure Colistin

The utility of this invention is based on finding that purified colistin, colistin component, a mixture thereof or any of its pharmaceutically acceptable salts are at least two or more times active against *Pseudomonas aeruginosa* than the currently used anti-*Pseudomonas aeruginosa* agent colimycin. This is particularly true when colistin or colimycin are administered in an aerosol.

A. Anti-*Pseudomonas aeruginosa* Activity of Colimycin

As already described above, colimycin is a sulfomethyl derivative of colistin conjugated with up to 5 moles of formaldehyde and 5 moles of sodium sulfite per mole colistin. It has also been described previously in *British J. Pharmacol.*, 23: 552–574 (1964) that sulfomethyl colistin derivatives are at least 20 fold less active against *Klebsiella pneumonia* when compared to colistin base, and that for their significant bioactivity they require hydrolysis to colistin base. For this reason it has been suggested that use of these derivatives for topical application is contraindicated.

Figure 15:
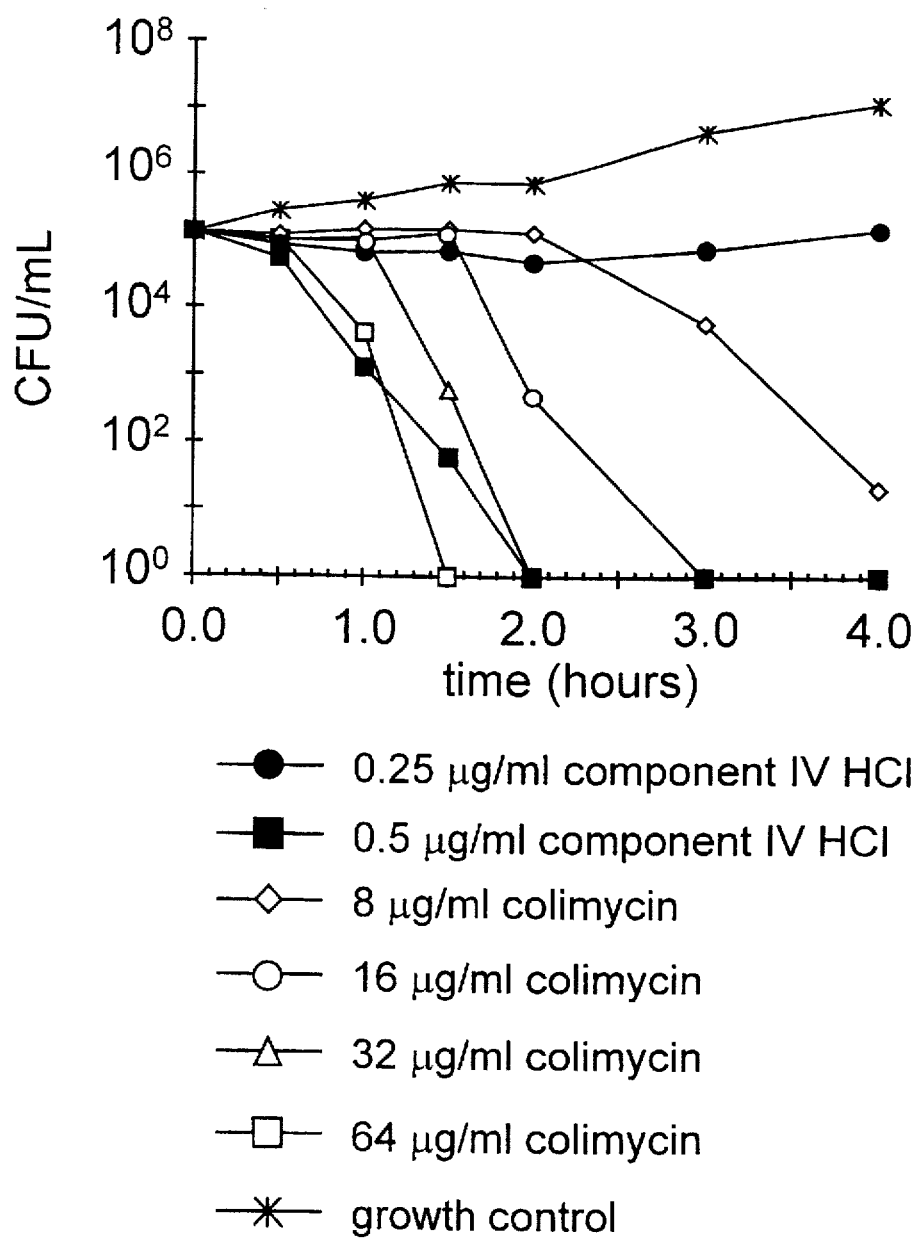

In order to confirm or refute these findings, bioactivities of parenteral colimycin and purified colistin component IV sulfate were compared by incubations of serial dilutions of freshly dissolved test articles against actively growing *Pseudomonas aeruginosa* strain 27853 according to Example 13. Results are seen in FIG. 15 and described below.

B. Anti-*Pseudomonas aeruginosa* Activity of Colistins

Anti-*Pseudomonas aeruginosa* activity of colistin or colistin components was investigated by determining the relative biological activities of components I, III, and IV and comparing these activities with the activity of colimycin.

Minimum inhibitory concentrations (MIC) of tested purified colistin components I, III, and IV sulfate salts, as well as purified colistin component IV hydrochloride against *Pseudomonas aeruginosa* ATCC 27853 were determined by broth microdilution method using inoculum, media, incubation conditions and end-point in accordance with approved standards of the National Committee for Clinical Laboratory Standards (NCCLS) according to Example 13.

For testing, stocks were prepared at 100X the final concentration and diluted in cation-adjusted Mueller Hinton broth in a serial two fold dilution. The tested colistin component was adjusted to a final inoculum of $10^5$ colony forming units per milliliter of test broth. Testing was performed in a microtiter tray with a final test volume of 100 microliters.

The quality assurance of testing was achieved by first testing *Pseudomonas aeruginosa* ATCC 27853 and *Escherichia coli* ATCC 25922 under identical conditions in cation-adjusted Mueller Hinton broth against ampicillin, gentamycin, and ciprofloxacin. Obtained results were accepted when MICs of these drugs were within the acceptable ranges published by the NCCLS. Testing of individual colistin components was performed under the same testing conditions.

Obtained results have shown that colistin components I, III and IV activities against *Pseudomonas aeruginosa* strain 27853 were not significantly different (by mass), with MIC values of between 0.5 and 1.0 µg/ml. In other words, all colistin components have shown qualitatively and quantitatively the same activity against *Pseudomonas aeruginosa*. This activity was observed to be comparable to the activity of the colistin sulfate U.S.P. from which fractions I, III, and IV were originally isolated, indicating that as seen in FIG. 8 any significant colistin sulfate would be suitable for aerosolization as a single entity.

C. Comparison of Anti-*Pseudomonas aeruginosa* Activities of Colimycin and Colistin Comparison of anti-*Pseudomonas aeruginosa* activities of colimycin and colistin hydrochloride was performed using time kill kinetic studies as described in *Antimicrobial Susceptibility Testing*, Section 5.16.: Tests to assess bactericidal activity, *Clinical Microbiology Procedure Handbook*, Ed. Henry D. Isenberg, ASM, Washington, DC (1992). The exact procedure is described in Example 14.

Briefly, tests were similar to those used for determining MICs, except that the final test volume was larger (10 mL) to allow sampling at various time points. Parenteral colimycin was freshly diluted immediately before testing. Cultures were incubated at 37° C. At initial set-up and at various time-points, cultures were plated, with or without further dilution, onto sheep blood agar plates. Plates were incubated for 18–24 hours, and the number of CFU/mL was determined and plotted to determine the percentage of surviving organisms and the time required to achieve 99.9% killing. Results are seen in FIG. 15.

FIG. 15 shows comparison of the anti-*Pseudomonas aeruginosa* bactericidal activity of colistin component IV hydrochloride and colimycin parenteral. In this study, *Pseudomonas aeruginosa* organisms were exposed to varying concentrations of colistin or colimycin as indicated in FIG. 15. Concentrations of colimycin were between 8–64 μg/ml. Concentrations of colistin component IV hydrochloride were 0.25 and 0.5 μg/ml, that is 32–256 (for 0.25 μg/ml) and 16–128 (for 0.5 μg/ml) times lower that concentrations of colimycin. Colony-forming unit (CFU) per ml were determined and plotted against drug exposure time in hours.

As seen in FIG. 15, a 0.5 μg/ml solution of purified colistin component IV hydrochloride was observed to kill over 5 logs of test organism within 2 hours of incubation. A similar level of killing by freshly dissolved colimycin required a 32 μg/ml solution, demonstrating that colistin component IV hydrochloride is approximately 64 times more potent by mass than freshly diluted parenteral colimycin. The only colimycin which showed such killing at 1.5 hours was the 128 times more concentrated solution of 64μg/mL colimycin. Colimycin of lower concentrations of 16 μg/mL achieved over 5 logs killing at 3 hours. Colimycin 8 μg/mL did not, even at 4 hours of testing, eradicate the *Pseudomonas aeruginosa* organism.

These studies clearly show the superiority of purified colistin over the currently used parenteral colimycin for aerosolization.

V. Colistin Aerosol Formulation

*Pseudomonas aeruginosa* is a bacterium residing in the lower respiratory tract. While it is possible to treat it with systemically administered drugs, such treatment is not especially effective, unnecessarily exposes the patient to large doses of the drug and may have other undesirable symptoms. The preferred treatment of *Pseudomonas aeruginosa* thus is by administration of aerosolized drug directly to the patients lungs.

As shown above, purified colistins are very effective against *Pseudomonas aeruginosa* in in vitro conditions. When preformulated as a pre-dissolved sterile solution ready for aerosolization, purified colistins are also very effective as aerosolized treatment of *Pseudomonas aeruginosa* in in vivo.

Aerosol formulation of the invention which is therapeutically effective in eradication of *Pseudomonas aeruginosa* pulmonary infection has several advantages over currently available colimycin aerosol treatments for *Pseudomonas aeruginosa*.

First, the current formulation comprises substantially purified colistin, a component thereof, a mixture of components or a salt thereof.

The preferred formulation contains a single, substantially, that is more than 95%, pure biologically active chemical colistin entity isolated from the commercially available colistin sulfate wherein the biological activity of the colistin is consistently standard and reproducible and is several folds higher than the biological activity of the currently available formulation of the prodrug colimycin.

Since the formulation contains only purified colistin, it allows the use of minimal but efficacious amount, typically from about 1 to about 50 mg/ml, of colistin formulated in a small volume, typically from about 2 to about 5 ml of physiologically acceptable aqueous solution, preferably ranging from full to half strength of isotonic saline so that the formulation is isotonic. Most preferably, about 1–50 mg/ml of colistin is formulated in 2–5 ml of full strength saline.

Additionally, the current formulation has a purity, salinity and pH in ranges permitting generation of a colistin aerosol without the presence of bronchial irritants such as formaldehydes or sulfites and is well tolerated by patients. The colistin formulation of the invention prevents the development of secondary undesirable side effects such as bronchospasm, bronchial irritations, chest pain and cough which are typically observed during administration of aerosolized colimycin. These symptoms are caused by high alkalinity evidenced by a rapid increase of pH in colimycin solution upon its dissolution, and also due to the presence of impurities in colimycin.

The aerosol colistin formulation is easily soluble in water in concentrated form in such a way that all or almost all colistin solution is nebulized into particle sizes which are delivered to the terminal and respiratory bronchioles where the *Pseudomonas aeruginosa* or *Stenotrophomonas maltophilia* bacteria resides.

The formulation is very stable even in a pre-dissolved sterile solution ready for aerosolization. The active compounds of the formulation, namely purified colistins, do not contain impurities or contaminants which dilute their biological activity and, therefore, the administered dosage is controllable and the highest degree of efficacy with lowest amount of drug is achieved. Due to colistin purification, the aerosol formulation does not cause secondary symptoms and complications described above. Additionally both overdosing or underdosing is prevented. The formulation is stable at optimal physiologically acceptable pH range between 6.0 and 7.0.

The current formulation, therefore, meets primary requirements for any aerosolized formulation, such as safety and efficacy as well as convenience and practicality of use, long-shelf life, storage and handling of the formulated products and overall low cost.

A. Specific Properties of Colistin Aerosol Formulation

The colistin formulation of the invention has a stable pH, does not foam during aerolization and because of its heat stability it allows easy sterilization. Once formulated, it is very stable.

1. Adjustment and Stability of pH

Determination of component IV stability at physiologic pH was made by dissolving purified colistin component IV sulfate or hydrochloride at a concentration of 20 mg/ml in sterile water containing 120 mM NaCl. The solution was mixed and pH was monitored. A 10N NaOH solution was used to adjust the solution pH to 6.95–7.00. Results are seen in FIG. 16.

FIG. 16 shows titration of colistin component IV sulfate and colistin component IV hydrochloride with NaOH to yield 20 mg/mL solutions of pH 6.9–7.0. As seen in FIG. 16, both colistin component IV salts show buffering capacity when brought to a physiologically acceptable pH of between 6.5 and 7.0. Once formulated at a certain pH, without addition of alkali, the pH of colistin solutions of the invention is stable and does not change, as seen in FIG. 10.

2. Foaming

Colimycin contains significant quantities of unidentified materials as already discussed above. For example, a typical 150 mg dose of dry powder for injection has an actual mass of over 400 mg and thus contains about 250 mg of materials other than it should. When this material is dissolved at colistin-equivalent concentrations above about 20 mg/ml, the solution is prone to significant foaming and sputtering, particularly when used in the jet nebulizer. This foaming reduces the amount of drug aerosolized and also has a tendency to clog the nebulizer.

3. Sterilization of Colistin Formulation

In order for a formulation in solution to have viable life-span and shelf-life, the solution is sterilized using any suitable sterilization technique, such as for example filtration through a 0.2 micron cellulose acetate filter. The solution was found stable even under high temperatures, therefore any type of sterilization which will not degrade the formulation and/or the active agent is advantageously utilized for sterilization of the preformulated solution of purified colistins.

4. Stability of Colistin Formulation

For practical purposes, it is preferred if aerosol formulations are premixed and provided in a ready-to-use form to the end-user so that the patient can use the formulation without need for making fresh solution, dealing with possible contamination and other such complications. The stability of premixed aerosol formulation is, therefore, an issue. For these reasons, long-term stability was therefore investigated.

Long-term stability of 20 mg/ml colistin component IV formulations was studied by incubating 0.4 ml aliquots in polyallomer screwcap microfuge tubes continuously at room temperature, 50° C., 60° C., 70° C., 80° C., and 90° C. Aliquots (0.1 mg) were analyzed at various incubation times up to 19 days by analytical HPLC. Results are seen in FIG. 17.

Figure 17:
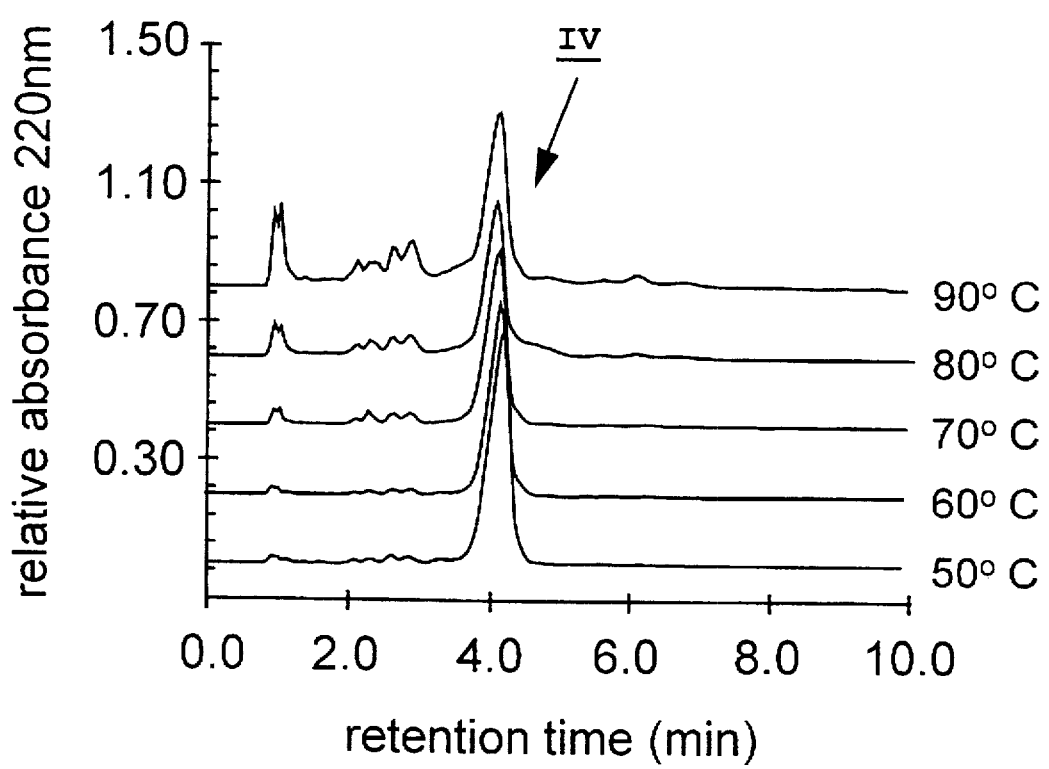

HPLC elution profiles seen in FIG. 17 demonstrate that the 20 mg/ml colistin component IV sulfate formulation at pH 6.9–7.0 is stable at 60° C. for 19 days, with the generation of trace degradation products visible at 70° C. at 19 days. The relative amounts of these degradation products were observed to increase as a function of incubation temperature between 70° C. and 90° C.

Assuming that a ten fold increase in temperature roughly corresponds to a stability increase of ten fold in time at lower temperatures, these data indicate that 20 mg/ml isotonic pH 6.9–7.0 colistin formulations are stable at room temperature at least for and in excess of 5 years.

B. Nebulization Characteristics of Preformulated Colistin and Colimycin

For successful preformulated aerosol formulation, it is also necessary that such a formulation may be easily aerosolized into particle sizes commensurate with the tissue to be treated. In the case of *Pseudomonas aeruginosa* and *Stenotrophomonas maltophilia*, the bacterium resides in the lower endobronchial space. It is therefore important to provide aerosol having a particle sizes which would be able to enter this space and deliver the drug there. For the endobronchial space, the aerosol particles must be no smaller than 2µ and no larger than 5µ having a MMAD between 2–5µ. For these reasons, nebulization conditions were investigated and the aerosol of the formulation was characterized.

1. Colistin and Colimycin Aerosol Formulation

Colimycin was freshly dissolved in 37.5 mM NaCl at a concentration of 20 mg/ml colistin base equivalent immediately prior to nebulization. Colistin component IV sulfate was dissolved in 120 mM sodium chloride, and the pH was adjusted to 7.0 with 1 molar sodium hydroxide.

2. Nebulization Conditions

Aerosolization of anti-*Pseudomonas aeruginosa* agents has the advantage of being able to deliver high concentrations of the active colistin or colimycin directly to the airways with low systemic absorption. This allows the development of a safer, long-term therapy. For this purpose, the nebulization conditions were investigated using a jet nebulizer.

Four ml of solution to be nebulized was placed in a Pari LC Jet nebulizer fitted with a Pulmonaide Compressor (DeVilbiss Model 5650D) with an air flow rate of 4–6 liters/minute. Aerosols generated are characterized by passing through a laser diffraction particle analyzer (Malvern Mastersizer X). Each formulation was analyzed multiple times to determine reproducibility of results, which were expressed as total obscuration time, mass median average diameter, and respirable fraction.

3. Colistin and Colimycin Aerosol Characterization

Figure 18:
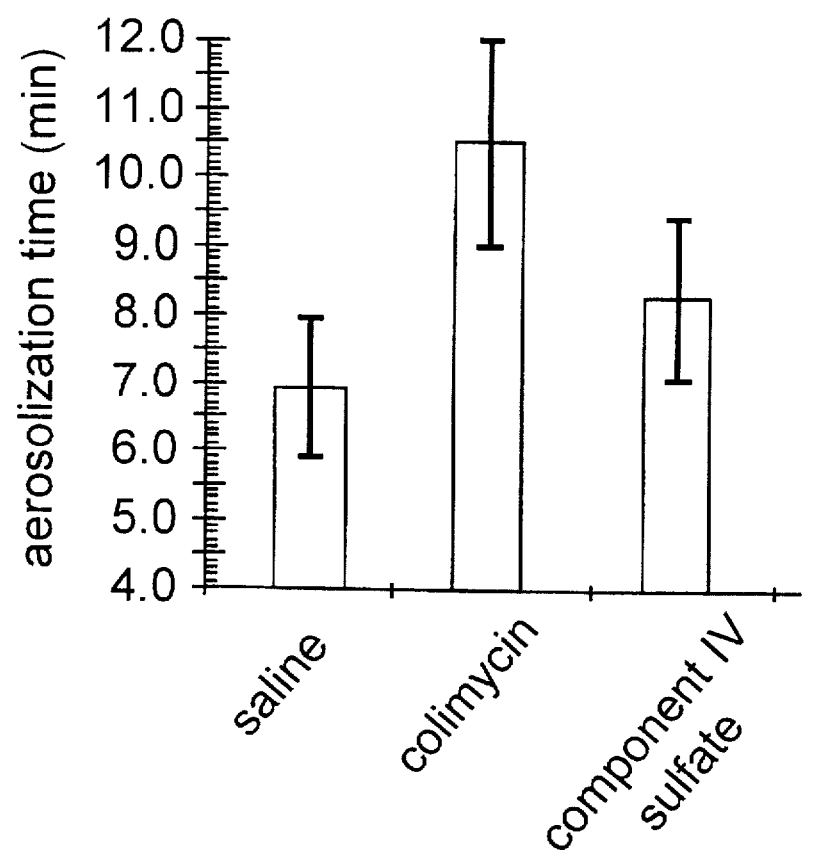

In order to characterize colistin aerosols, and to investigate differences between the colimycin and colistin aerosol formulations, comparisons of the aerosolization of 150 mM (isotonic) NaCl alone, 20 mg/ml colistin component IV sulfate in 120 mM or 20 mg/ml colimycin in 39.5 mM NaCl were made. Results are shown in FIG. 18, which is a comparison of the times required for aerosolization of 4 mL of the three solutions. The two drug solutions were analyzed three times, and saline was analyzed four times. Bars show standard deviations of measurements. Results seen in FIG. 18 demonstrated that mean aerosolization times were different for the three entities. Aerosolization of saline controls was achieved in an average of 6.92 minutes (standard deviation of 1.22 minutes, n=4). Aerosolization of isotonic pH balanced 20 mg/ml colistin component IV sulfate was achieved in 8.31 minutes (standard deviation of 1.12 minutes, n=3) compared to colimycin 20 mg/mL formulated in ¼N saline which was aerosolized in 10.53 minutes (standard deviation 1.49 minutes, n=3).

Mass median particle diameters of the aerosol, expressed as average±standard deviation (n) for each of the aerosols were 4.57±0.13 microns (4), 4.30±0.13 (3), and 4.11±0.29 (3) for saline, colistin component IV sulfate, and colimycin, respectively. Average respirable fractions of the aerosols, which are expressed as average percentage of particles ranging from 1 micron to 6 microns in diameter within the aerosol over time, were 57.00±2.71 (4), 58.90±1.56 (3), and 58.77±2.03 (3) for saline, colistin component IV sulfate and colimycin, respectively.

4. Nebulizers

Prior art aerosolized colimycin formulations containing higher concentrations of the drug (150 mg/ml or greater) were not very efficiently nebulized for various reasons discussed above.

An indivisible part of this invention, therefore, is a selection of a nebulizer able to nebulize the formulation of the invention into aerosol particle size in the range from 1–5μ.

While the range variety of nebulizers is available, only a limited number of these nebulizers are suitable for the purposes of this invention.

To identify efficient and suitable nebulizer for use in the current invention, investigation of available nebulizers was made to determine in vitro which nebulizers meet criteria that are important for delivery of aerosolized colistins. Both ultrasonic and jet nebulizers are suitable.

Two types of nebulizers, such as jet and ultrasonic nebulizers are currently available, which can produce and deliver particles between the 1 and 5μ particle sizes that are optimal for treatment of *Pseudomonas aeruginosa* infections. A jet nebulizer works by air pressure to break a liquid solution into aerosol droplets. An ultrasonic nebulizer works by a piezoelectric crystal that shears a liquid into small aerosol droplets. However, only some formulations can be efficiently nebulized by both nebulizers as both devices are sensitive to the pH of the formulation and to its ionic strength.

The major limitation of the ultrasonic Ultraneb 99 (DeVilbiss) ultrasonic nebulizer used for delivery of colistin formulation are its high-cost, waste of the drug and inconvenience. As seen from Table 1, this nebulizer requires 30 ml of the drug solution, and it has large, 1200 ml aerosol reservoir. In order for colistin aerosol therapy to be widely available and used by patients in ambulatory or home setting, a more efficient and easier to use nebulizer is needed.

Comparative characteristics of the Ultraneb 99 DeVilbiss (ultrasonic) and two jet nebulizers, the Sidestream and the Pari LC with the PulmoAide compressor, are listed in Table 1.

TABLE 1

Comparative Characteristics of Different Nebulizers

| Nebulizer | DeVilbiss 99 | Sidestream | Pari LC |
|---|---|---|---|
| Type | Ultrasonic | Jet | Jet |
| Airflow | 8 L/m | 8 L/m | 8 L/m |
| Liquid Reservoir | 30 ml | 5 ml | 5 ml |
| Time to Nebulize | 10–12 minutes | ~13 minutes(*) | 10 minutes(**) |
| Aerosol Reservoir | 1,200 ml | 30 ml | 30 ml |
| MMAD** | ~4–5 microns | ~2.2 microns | ~4–5 microns |

*Time to sputtering of jet
**Mass median aerodynamic diameter

As seen from Table 1, there are substantial differences between the ultrasonic and jet nebulizer systems. The two jet nebulizers require about six times smaller solution volume and do not require a large reservoir from which the aerosol can be inhaled.

Of the two jet nebulizers compared in Table 1, the Sidestream may be more efficient in delivery colistin to the lower airway because of the smaller (2.2μ) particle size output. Conversely, the Pari LC produces a larger particle size (4.5μ) at a higher output thus reducing the delivery time and patient's discomfort. Both jet nebulizers have a Venturi design which increases drug delivery within inspiration. The smaller equipment size decreases the fallout of aerosolized particles that occurs prior to inspiration by the patient. The jet nebulizers Sidestream and Pari LC also have the advantage of being available in both reusable disposable units.

In addition to the above jet nebulizers, two small volume ultrasonic nebulizers, Aerosonic by DeVilbiss and UltraAire by Omron are also suitable for delivery of the formulation of the invention. These ultrasonic nebulizers differ from the UltraNebb 99 ultrasonic as they have a smaller reservoir and can use the smaller volume solution.

VI. Colistin Dry Powder Formulation

Unique properties of the current invention include ability of colistin to be formulated and delivered as a dry powder. Colistin dry powder formulation of the invention is based on the finding that purified colistin or its components have a very high therapeutic potency and are therefore therapeutically effective in such low dosages that the delivery of the dry powder is possible.

A. Dry Powder Formulation

For dry powder formulation of the invention, purified colistin, a purified colistin component, and admixture thereof, or a pharmaceutically acceptable salt thereof is milled to a powder having mass median average diameters ranging from 1–5 microns by media milling, jet milling, spray drying or particle precipitation techniques. Particle size determinations are made using a multi-stage Anderson cascade impactor or other suitable method.

Media milling is accomplished by placing drug substance into a mill containing, for example, stainless steel or ceramic balls and rotating or tumbling the material until the desired drug particle size ranges are achieved. Advantages of media milling include good size control, narrow product size ranges, high efficiencies of recovery, and readily scalable processes. Disadvantages include long process times (on the order of hours to days), the requirement that the milling media be separated from the product at completion, and the possibility of contamination of the product with the media.

Jet milling uses very high pressure air streams to collide particles with one another, with fine particles of the desired size being recovered from the mill. Advantages include rapidity (seconds to minutes for completion) and less energy transfer during milling resulting in less temperature rise of drug product. Disadvantages include poorer collection efficiencies (50 to 80% recovery is typical).

Both techniques and any and all improvements thereof are intended to be within the scope of the invention.

Spray drying is achieved by spraying a fine mist of drug solution onto a support and drying the particles. The particles are then collected. Spray drying has the advantage of being the least prone to degrading chemical entities.

Solution precipitation is performed by adding a co-solvent which decreases the solubility of a drug to a uniform drug solution. When sufficient co-solvent is added, the solubility of the drug falls to the point where solid drug particles are formed which can be collected by filtration or centrifugation. Precipitation has the advantage of being highly reproducible and can be performed under low temperature conditions which reduce degradation.

The colistin dry powder prepared as described above in dosages from 1–100 mg, preferably from 1–10 mg of dry powder, is used directly in metered dose or dry powder inhalers.

B. Metered Dose Inhalers

A metered dose inhaler consists of three components: a canister containing the propellant/drug suspension, a metering valve designed to deliver accurately metered volumes of the propellant suspension, and an oral adapter which contains a spray orifice from which the metered dose is delivered. In the rest position the metering chamber of the valve is connected to the drug suspension reservoir via a filling groove or orifice. On depression of the valve this filling groove is sealed and the metering chamber is exposed to atmospheric pressure via the spray orifice in the oral adapter and the valve stem orifice. This rapid pressure reduction leads to flash boiling of the propellant and expulsion of the rapidly expanding mixture from the metering chamber. The liquid/vapor mixture then enters the expansion chamber, which is constituted by the internal volume of the valve stem and the oral adapter. The mixture undergoes further expansion before being expelled, under its own pressure, from the spray nozzle. On exit from the spray orifice, the liquid ligaments which are imbedded in propellant vapor are torn apart by aerodynamic forces. Typically, at this stage the droplets are 20 to 30 micron sin diameter and are moving at the velocity of sound of the two-phase vapor liquid mixture (approximately 30 meters/second).

As the cloud of droplets moves away from the spray nozzle, it entrains air from the surroundings and decelerates, while the propellant evaporates through evaporation, the entrained droplets eventually reach their residual diameter. At this point, the particles/droplets consist of a powdered drug core coated with surfactant. Depending on the concentration and the size of the suspended material the powdered drug core can consist of either individual drug particles or aggregates.

Currently, metered dose inhaler technology is optimized to deliver masses of 80 to 100 micrograms of drug, with an upper limitation of 1 mg of drug deliverable. The discovery of a more potent formulation of colistin, colistin components, mixtures thereof, or pharmaceutically-acceptable salts thereof enables metered dose inhaler technology to become a vehicle of choice for colistin delivery.

C. Dry Powder Inhalers

An alternate route of dry powder delivery is by dry powder inhalers.

There are two major designs of dry powder inhalers, device-metering designs in which a reservoir of drug is stored within the device and the patient "loads" a dose of the device into the inhalation chamber, and factory-metered devices in which each individual dose has been manufactured in a separate container. Both systems depend upon the formulation of drug into small particles of mass median diameters form 1 to 5 microns, and usually involve coformualtion with larger excipient particles (typically 100 micron diameter lactose particles). Drug powder is placed into the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs.

Current technology for dry powder inhalers is such that payload limits are around 10 mg of powder (of which drug is usually a minor component by mass). The discovery of a formulation of colistin, colistin components, mixtures thereof, or pharmaceutically-acceptable salts thereof that is several fold more potent than currently aerosolized colimycin allows dry powder inhaler technology to become a preferred delivery vehicle for colistin dry powder.

UTILITY

The formulation of the invention is suitable for delivery of an efficacious amount of the purified colistin, its components or its pharmaceutically acceptable salts sufficient for treatment and prophylaxis of acute and chronic *Pseudomonas aeruginosis* infections. The novel formulation has a small volume yet delivers an effective dose of colistin to the site of the infection.

Cystic fibrosis patients and other patients with chronic endobronchial infections caused by *Pseudomonas aeruginosis* or *Stenotrophomonas maltophilia* have a high incidence of bronchospastic reactions. Their airways are therefore very sensitive to hypotonic or hypertonic aerosols, to the presence of a permanent ion, as well as to aerosols that are acidic or basic. The effects of irritating the airways can be clinically manifested by cough or bronchospasm, both of which conditions prevent efficient delivery of aerosolized colistin into the endobronchial space. It is therefore of importance that the current aerosol formulation does not provoke these conditions.

EXAMPLE 1

Analytical HPLC of Colistin Components

This example illustrates a chromatographic procedure used for characterization of colistin components.

Colistin Sulfate U.S.P., non-sterile oral powder Lots A1620275, A11620277, A1620278, A1620273 or A1620280 obtained from Dumex, Ltd., Denmark, was dissolved in deionized water at a concentrations ranging from 10 mg/ml for analytical HPLC to 300 mg/ml for preparative HPLC. Samples were filtered through 0.45 micron syringe-end cellulose acetate filters and stored at 4° C. between uses.

Ten microliters containing 100 µg of colistin sulfate U.S.P. were injected onto either a 4.6 mm diameter×150 mm length Vydac 218TP C-18 reverse phase or a 4.6 mm diameter×150 mm length Beckman Ultrasphere ODS C-18 reverse phase high performance liquid chromatography (HPLC) column and eluted with 2.0 ml per minute of 23% acetonitrile and 77% 105 mM ammonium sulfate, pH 2.0 using a Beckman System Gold programmable solvent module #126. Eluate was monitored by absorbance at 220 nm by UV detector using Beckman Diode Array detector module 168. Ammonium sulfate running buffer, pH 2.0 was prepared by adding concentrated sulfuric acid to a 50 mM aqueous solution of ammonium sulfate while monitoring pH using a Beckman Phi-10 pH meter and a Beckman Futura Plus combination electrode calibrated with pH 4.0 and 7.0 buffers according to manufacturer's instructions. Elution profiles for each colistin sulfate lot were obtained and compared with other lots, as well as with literature profiles for colistin sulfate HPLC.

EXAMPLE 2

Isolation and Characterization of Major Colistin Sulfate Components

This example describes procedures used for isolation and characterization of major components of colistin sulfate.

Fractions of the colistin sulfate components I, III and IV were obtained by preparative HPLC of colistin sulfate U.S.P.

Component separation was performed on a reverse-phase preparative column (Prep Nova-Pak HR C18 40×100 mm cartridges) obtained from Waters Corporation was performed using a mobile phase of 23% acetonitrile (High Purity Acetonitrile UV) obtained from Burdick & Jackson and 77% 105 mM ammonium sulfate, pH 2.0.

Three hundred mg of colistin sulfate U.S.P. (Dumex, Ltd., Denmark) previously dissolved in 1.0 mL deionized water was separated at a flow rate of 20 ml/min. Product elution was followed by UV detector set at 200 nm. Fractionated components I (100 ml), III (50 mL), and IV (300 mL) solutions were reduced to dryness by rotoevaporation. Compounds were extracted from inorganic salts by dissolution in 50 mL pure methanol, which was filtered into a separate vessel. Relative amounts of colistin in each fraction were determined by assuming that each entity had an extinction coefficient equivalent to that previously determined for component IV.

Amino acid analysis was performed on component I, III and IV following 20 hour hydrolysis at 115° C. in 6N HCl, 0.05% mercaptoethanol, 0.02% phenol as described above in Section I.A.

Ion-spray mass spectroscopy of components I, III and IV was performed according to method described in Example 8. Five microliters of a 333 micrograms/ml solution of purified colistin component sulfate salt (1.6 micrograms) was injected onto an small C-18 reverse phase C-135-B guard column from Upchurch Scientific, coupled to a Finnigan SSQ 7000 mass spectrometer. The sample was eluted off the column at 0.5 ml/min in 30:70 acetonitrile/water containing 0.1% acetic acid and analyzed by positive ion electrospray as seen in FIG. 12.

Dried fractions of components I, III and IV were suspended in sterile irrigation water at concentrations of approximately 5 mg/ml and filtered through a 0.45 micron syringe-end cellulose acetate filter. The abilities of components I, III and IV solutions to rotate plane-polarized light from the sodium D line at 589 nm wavelength were determined using a Perkin-Elmer 241 polarimeter and a 1 dcm cuvette at 25° C. Normalized rotations were obtained by dividing observed rotations by compound concentrations expressed in grams/mL. The values were expressed as rotation in degrees.

NMR spectrometry was performed to determine the individual compositions of each component. For that purpose, 15 mg of dried fractions of component I, III and IV were suspended in 0.5 mL volumes of $D_2O$ contains 99.9% D, obtained from Cambridge Isotope Laboratories, Woburn MA for $^{13}C$ NMR spectroscopy. Sodium 3-(trimethylsilyl) propionate-2,2,3,3-d4 (98%) obtained also from Cambridge Isotope Laboratories was added as an internal standard. At least 200,000 acquisitions for each compound were made on a General Electric model QE-300 NMR spectrometer with a Nicolet 1280 date processor at an observed frequency for $^{13}C$ of 75.5 Mhz, a tip angle of 29.66 degrees, a recycle time of 181 msec, and spectrum width of 10000 Hz.

Representative $^{13}C$-NMR spectra for component I, III and IV are shown in FIG. 7 and were described above.

NMR spectra for component I detected the following values, (carbon-13 NMR, ppm in $D_2O$): 175.81, 175.65, 175.54, 175.08, 174.97, 174.30, 69.88, 69.31, 68.97, 62.57, 62.54, 61.93, 56.09, 55.96, 55.93, 55.01, 54.97, 54.66, 54.61, 54.56, 54.53, 54.49, 54.36, 54.21, 54.17, 54.06, 53.78, 53.65, 39.59, 39.48, 39.40, 39.33, 39.31, 38.38, 31.54, 31.51, 31.47, 31.40, 31.20, 31.08, 29.92, 28.92, 28.27, 27.38, 27.32, 27.26, 25.17, 24.73, 24.68, 23.98, 23.24, 23.18, 22.04, 21.67.

NMR spectra for component III detected the following values. (carbon-13 NMR; ppm in $D_2O$): 177.64, 177.30, 177.19, 175.76, 175.60, 175.25, 175.04, 174.99, 174.81, 174.65, 174.27, 69.87, 69.49, 62.60, 61.92, 55.79, 54.91, 54.64, 54.59, 54.37, 54.19, 54.07, 53.86, 53.82, 39.63, 39.43, 39.32, 38.38, 38.22, 36.41, 31.65, 31.48, 28.67, 28.33, 27.32, 27.25, 25.13, 24.75, 24.68, 23.97, 23.78, 22.04, 21.98, 21.65, 21.44, 18.11, 13.40, 13.06.

NMR spectra for component IV detected the following values. carbon-13 NMR (ppm in $D_2O$): 180.33, 177.66, 177.32, 176.07, 175.73, 175.58, 175.51, 175.04, 174.93, 174.58, 174.23, 69.78, 69.15, 62.41, 61.78, 55.97, 55.8, 54.78, 54.55, 54.4, 54.03, 53.91, 53.58, 42.48, 41.81, 39.42, 39.23, 39.14, 38.82, 38.26, 38.11, 36.3, 33.33, 32.46, 31.58, 31.46, 31.4, 31.07, 31.03, 28.54, 28.28, 27.19, 27.14, 25.11, 24.55, 23.83, 22.99, 21.94, 21.55, 21.34, 13.36.

EXAMPLE 3

Determination of the Relative anti-Pseudomonal Activities of Colistin Sulfate U.S. P. Components This example describes the method used to compare the ability of different fractions of colistin sulfate to inhibit the growth of *Pseudomonas aeruginosa*.

A 100 microgram (50 ul) sample of colistin sulfate U.S.P. was injected onto an analytical HPLC column and eluted at 2.0 ml/min with 23% acetonitrile, 77% ammonium sulfate, pH 2.0. Beginning at 1.0 minute, fractions were collected into 1.5 ml snap-cap centrifuge tubes at 0.2 minute intervals using a Gilson FC 203B fraction collector. A total of 20 fractions of 0.4 ml volume were collected from elution time 1.0 minutes to 5.0 minutes. The volume of tubing between the UV detector cell and the fraction collector was determined to be 0.4 ml, so that fraction #1 corresponded to that region of the UV trace between 0.8 and 1.0 minutes. Each fraction was dried by Savant SC110A vacuum concentrator, suspended in 0.4 ml growth media, and filter sterilized.

A series of 2-fold dilutions of each sterile resuspended fraction was made into sterile growth media, and the abilities of each dilution to inhibit the growth of *Pseudomonas aeruginosa* strain 27853 was determined by surveying culture turbidity after incubation at 18 hours at 37° C. Minimum inhibitory concentrations were defined as the lowest dilution of a fraction at which turbidity was inhibited.

EXAMPLE 4

Preparative HPLC Fractionation for Purification of Colistin Component IV

This example describes procedure used for substantial purification of colistin component IV.

Colistin component IV is the major of colistin sulfate U.S.P. by weight, as determined by analytical HPLC described in Examples 1 and 3.

Colistin component IV sulfate was purified to greater than 95% purity by preparative HPLC.

A reverse-phase preparative column, Prep Nova-Pak HR C18 40×100 mm cartridge, was run using a mobile phase of 23% acetonitrile and 77% 105 mM ammonium sulfate, pH 2.0. 100 to 300 mg of colistin sulfate U.S.P. previously dissolved in deionized water was separated at a flow rate of 20 ml/min, and product elution was followed by UV detector set at 220nm. Eluate was collected from 16 minutes to 23 minutes. Pooled collected fractions were re-injected on an analytical reverse-phase HPLC column to verify product purity, as seen in FIG. 12.

EXAMPLE 5

Desalting of Fractionated Colistins

This example describes procedure used for desalting of fractionated colistins.

Colistin component IV was extracted from the pooled eluates by reducing the volume of the fraction which consisted of 23% acetonitrile and 77% 105 mM ammonium sulfate, at pH 2.0, 10 fold with a Buchi R-114 rotary evaporator. Concentrated material containing 1.0 gram of colistin component IV, as determined spectrophotometrically by absorbance at 220nm of serial dilutions, was loaded onto a 3 cm×22 cm glass BioRad chromatography column packed with C-18 reverse phase resin (Whatman LRP-2, Lot 03035) previously washed with 4 void volumes of acetonitrile followed by 4 void volumes of deionized water. Solvents, passed through the column via peristaltic pump running at 1 ml/min and 9 ml fractions, were collected in Kimax borosilicate 13×100 mm tubes. After loading the 1.0 gram of fractionated colistin component IV onto the column, the resin was washed with 1 void volume of irrigation water and eluted with 50 ml of 40% acetonitrile in water.

Fractions were assayed for colistin content by spotting 2 microliter aliquots onto a silica G thin layer chromatography plate, drying, spraying with a 0.75% solution of ninhydrin obtained from Mallinckrodt in 100% ethanol, and heating the plate to 100° C. The presence of a purple color due to reaction of ninhydrin with amino groups was taken as positive identifier for primary alkyl amines, including colistin. Ninhydrin-positive fractions were pooled, dried by Buchi R-114 rotary evaporator, dissolved in sterile irrigation water, transferred to a clean, pre-weighed 20 ml glass screwcap vial, frozen on dry ice, and lyophilized to dryness.

A typical desalting reaction yielded about 650 mg of dry colistin component IV sulfate for each 1.0 gram loaded on desalting resin. The absorbance spectrum of purified material was obtained using a Beckman DU spectrophotometer and 1 cm path length quartz cuvettes. A 1.0 mg/ml sample was scanned from 200 nm to 500 nm at a scan speed of 600 nm/min (FIG. 5). The extinction coefficient at 220 nm was determined by serial dilutions of the 1.0 mg/ml colistin component IV sulfate into water. A relatively linear relationship between concentration and optical density at 220 nm was observed up to 0.5 mg/ml (FIG. 4). Solutions greater than 0.5 mg/ml require dilution for accurate quantitation by spectrophotometry. Elemental microanalysis of the product after drying for 8 hours at room temperature was C 41.16%, H 7.77%, N 14.59%, S 5.77%, and $H_2O$ 5.34%. This composition is consistent with a solid containing 3 moles of sulfate and 5 moles of water per mole of component IV (Theoretical composition: C 40.97%, H 7.53%, N 14.42%, O 30.89% S 6.19%, $H_2O$ 5.79%, molecular formula $C_{53}H_{118}N_{16}O_{30}S_3$ and formula weight 1553.8 grams/mole).

EXAMPLE 6

Precipitation of Colistin Free Base

This example describes an alternate strategy to desalting purified colistin fractions.

NaOH (1N) was added dropwise to concentrated fractions column until the solution pH reached 11.0 as determined by Beckman Phi-10 pH meter and Futura Plus combination electrode. A precipitate formed which was collected by centrifugation in 35 ml "Oak Ridge" style polyallomer tubes at 25,000×g for 15 minutes in a Beckman J2-MI refrigerated centrifuge using a Beckman JA-20 rotor. The precipitate was washed twice with one volume of cold water and dried under vacuum for at least 24 hours.

Titration of this material using 1.0M HCl suggested that the complete colistin free base was not uniformly produced by this procedure, and also that residual NaOH was not completely removed by this process. In addition, the overall yield of this procedure was lower, averaging 200 to 300 mg recovery per gram of fractionated colistin sulfate.

EXAMPLE 7

Exchange of Colistin Salt Counterions

This example illustrates preparation of colistin salts by exchanging counterions.

Purified colistin component IV sulfate (1.2 grams) was dissolved in 50 ml of 2.0M $NaH_2PO_4$. The solution was passed over a C-18 reverse phase desalting chromatography column as described in Example 6, followed by 60 ml of deionized water. The column flow rate was maintained at 0.875 ml/min throughout. Seven milliliter fractions (collected every 8 minutes) were collected. Elution of colistin component IV phosphate was achieved with 100 ml of 40% acetonitrile/water and monitored by ninhydrin assay of 2 µl fractions on silica G TLC plates. Fractions containing colistin component IV phosphate (21–27) were pooled and derived by rotoevaporation. The solid was suspended in 10 ml deionized water, filtered through a 0.45 micron cellulose acetate filter, transferred to a pre-weighed 20 ml glass screwcapped vial, frozen with dry ice, and lyophilized for 72 hours. Approximately 700 mg of material was obtained. Elemental analysis showed a composition of C 37.46%, H 7.28%, N 13.05%, P 10.12%, S 0.16%, and $H_2O$ 3.12%, consistent with a solid containing approximately 5 moles of phosphate and 3 moles of water per mole of colistin component IV (theoretical composition C 37.15%, H 7.12%, N 13.08% 0 33.61%, P 9.04%, $H_2O$ 3.15%, molecular formula $C_{53}H_{121}N_{10}O_{36}P_5$ and formula weight grams/mole). The 0.16% observed sulfur content correlates to a remaining 0.003 moles of sulfate per mole component IV, indicating the efficiency with which phosphate was substituted for sulfate in this procedure (>99%). Analytical HPLC analysis of component IV phosphate confirmed that the composition of the solution remained intact during the desalting process (FIG. 13).

EXAMPLE 8

Mass Spectral Characterization of Purified Colistin Component IV Sulfate

This example describes mass spectrometric characterization.

Five microliters of a 333 micrograms/ml solution of purified colistin component IV sulfate (1.6 micrograms) was injected onto an small C-18 reverse phase C-135-B guard column from Upchurch Scientific, coupled to a Finnigan SSQ 7000 mass spectrometer. The sample was eluted off the column at 0.5 ml/min in 30:70 acetonitrile:water containing 0.1% acetic acid and analyzed by positive ion electrospray as seen in FIG. 12.

EXAMPLE 9

Gravimetric Titration of Purified Colistin Component IV

This example describes gravimetric titration of purified colistin component IV.

In order to determine the pKa of colistin component IV by titration, 107 mg of dry free base was suspended in 10.7 ml of deionized water in a 20 ml glass screwcap vial and stirred by magnetic stirrer. A calibrated Beckman Phi-10 pH meter with a Futura Plus combination electrode was placed in the suspension and the pH of the solution was monitored during the addition of 1.21M HCl. The starting pH of the suspension was observed to be 11.47, and 2 inflection points were observed during the titration, one at 40 micromoles of HCl added and a pH of 10.2 and a second at 505 micromoles of HCl added and a pH of 4.5. The first inflection point is inferred to identify neutralization of trace amounts of NaOH remaining in the solid material (40 micromoles×40 micrograms/micromol=1.6 mg or about 1.5% by weight). This is also consistent with the solution pH, since 40 micromoles hydroxide ion in 10.7 ml=3.75e-3 molar hydroxide. Since $[H+]\times[OH-]=1e-14$, the proton concentration would be 2.67e-12, and since pH=-log[H+], pH=-log (2.67e-12)=11.57, fairly close to the observed pH of the colistin component IV base suspension of 11.47.

The second inflection point represents the complete protonation of colistin component IV. The pKa of component IV in this experiment was observed to be approximately 9.0.

EXAMPLE 10

Determination of Impurities Mass Present in Colimycin M

This example shows determination of impurities mass or nonactive material present in the colimycin formulation.

To determine the actual mass of material present in this formulation, vials of commercially obtained colimycin were opened and the dry contents were immediately weighed in a pre-weighed plastic weigh-boat placed on a Mettler Top Loading Balance.

The following data were obtained:

Vial 1: Colimycin (Coly-Mycin M Parenteral, Parke-Davis, lot# 01966P) contained 399.0 mg.

Vial 2: Colimycin (Coly-Mycin M Parenteral, Parke-Davis, lot# 01966P) contained 405.0 mg.

Vial 3: Colimycin (Coly-Mycin M Parenteral, Parke-Davis, lot# 01966P) contained 402.9 mg.

The average mass contained in these three Parke-Davis Coly-Mycin M Parenteral vials was determined to be 402.3 mg of colimycin, representing an average excess in mass of 177.9 mg over the theoretical dosage of 224.4 grams of colimycin which should have been present according to product activity.

EXAMPLE 11

Determination of Colimycin Solution pH

This example describes the procedure used for determination of pH in colimycin solutions following dissolution.

The pH of freshly dissolved colimycin was determined by weighing a freshly opened vial of Coly-Mycin M Parenteral, Parke-Davis, lot# 01966P, containing 405 mg into 20 ml glass screwcap scintillation vials and adding an appropriate volume of sterile irrigation water to achieve 10.0 mg/ml, 15.0 mg/ml, and 20.0 mg/ml solutions. These values correspond to concentrations of 3.7 mg/ml, 5.6 mg/ml and 7.4 mg/ml colistin base equivalent. Solution pH was then monitored continuously using a Beckman Phi-10 pH meter fitted with a Beckman Futura Plus combination electrode calibrated at pH 4.0 and 7.0 as per manufacturer's instructions prior to use. At various times from 1 minute to 180 minutes, pH values and times were recorded.

EXAMPLE 12

Determination of Complexity of Colimycin

This example describes the procedure used for determination of colimycin components.

In order to characterize the complexity of colimycin solutions, 150 mg of colistin base equivalent of colimycin (Coly-Mycin M Parenteral, Parke-Davis, lot# 01966P), containing 402.9 mg was dissolved in 10 ml of 105 mM ammonium sulfate buffer, pH 2.0. The low pH of this solvent was predicted to rapidly hydrolyze the sulfomethyl conjugate of colistins.

At various time points after dissolution, 10 microliter aliquots equivalent to 150 micrograms of colistin base were injected onto a 4.6 mm diameter×150 mm length Vydac 218TP C-18 reverse phase high performance liquid chromatography (HPLC) column and eluted with 2.0 ml per minute of 23% acetonitrile and 77% 105 mM ammonium sulfate, pH 2.0 using a Beckman System Gold programmable solvent module #126. Eluate was monitored by absorbance at 220 nm by UV detector as described above. Ammonium sulfate running buffer (pH 2.0) was prepared by adding concentrated sulfuric acid to a 50 mM aqueous solution of ammonium sulfate while monitoring pH using a Beckman Phi-10 pH meter and a Beckman Futura Plus combination electrode calibrated with pH 4.0 and 7.0 buffers according to manufacturer's instructions.

EXAMPLE 13

Antibacterial Activity Testing of Colistin

This example illustrates testing of relative biological activities of colistin component I, III, and IV.

Minimum inhibitory concentrations (MIC) of test materials colistin component I, III, and IV as well as purified colistin component IV sulfate and colistin component IV hydrochloride, against *Pseudomonas aeruginosa* ATCC 27853 were determined by broth microdilution method using inoculum, media, incubation conditions and end-point in accordance with approved standards of the National Committee for Clinical Laboratory Standards (NCCLS) *Antimicrobial Susceptibility Testing*, Section 5.2, Broth Microdilution MIC testing, in *Clinical Microbiology Procedure Handbook*, Editor Henry D. Isenberg, ASM, Washington, DC., (1992); National Committee for Clinical Laboratory Standards; *Methods for Dilution Antimicrobial Susceptibility Tests for Bacteria that Grow Aerobically*, 3rd Ed. Approved standard M7-A-3, Villanova, Pa., (1993).

Stocks were prepared at 100× the final concentration and diluted in cation-adjusted Mueller Hinton broth in a serial two fold dilution. The test organism was adjusted to a final inoculum of $10^5$ colony forming unit per milliliter of test broth. Testing was performed in microtiter tray with a final test volume of 100 microliters.

Quality assurance of the testing was strictly followed. *Pseudomonas aeruginosa* ATCC 27853 and *Escherichia coli* ATCC 25922 were tested under identical conditions in cation-adjusted Mueller Hinton broth against ampicillin, gentamycin, and ciprofloxacin. Result were accepted when MICs of these drugs were within the acceptable ranges published by the NCCLS (ibid).

EXAMPLE 14

Comparison of Activities of Colimycin and Colistin Component IV Hydrochloride

This example describes the procedure used for determination and comparison of anti-*Pseudomonas aeruginosa* activity of colistin component IV hydrochloride and prodrug colimycin.

Time kill kinetic studies were performed as described in (*Antimicrobial Susceptibility Testing*, Section 5.16. Tests to assess bactericidal activity, in *Clinical Microbiology Procedure Handbook* (supra).

Tests were set in the same way used for determining MICs (Example 13), except that the final test volume was larger (10 mL) to allow sampling at various time points. Cultures were incubated at 37° C. At initial set-up and at various desired time-points, cultures were sampled and plated (with or without further dilution) onto sheep blood agar plates. Plates were incubated for 18–24 hours, and the number of CFU/mL was determined and plotted to determine the percentage of surviving organisms and the time required to achieve 99.9% killing.

EXAMPLE 15

Formulation of an Isotonic Colistin Component IV Solution for Aerosolization

This example describes procedures used for preparation of an isotonic colistin component IV formulation for aerosolization.

Purified dried colistin component IV sulfate or colistin component IV hydrochloride were dissolved at a concentration of 20 mg/ml in 120 mmol sodium chloride. The solution was mixed by magnetic stirring bar and the solution pH was monitored by a calibrated Beckman Phi-10 pH meter and Beckman Futura Plus combination electrode. A 10N NaOH solution was used to adjust the solution pH to between 6.95–7.00.

The solution was then sterilized by either filtration through a 0.2 micron cellulose acetate filter attached to a 10 ml syringe, or by autoclaving at 121° C. for 20 minutes. The integrity of sterilized solutions was determined by monitoring solution absorbance at 220 nm and by analytical HPLC profile as described in Example 1.

EXAMPLE 16

Long-term Stability of Colistin Formulation

This example illustrates determination of long-term stability and shelf-life of the colistin formulation.

Long-term stability of the colistin IV formulations was determined by incubating 0.4 ml aliquots in 0.6 ml polyallomer screwcap microfuge tubes continuously at room temperature, 50° C., 60° C., 70° C., 80° C., and 90° C. 0.1 mg aliquots were analyzed at various incubation times up to 19 days by analytical HPLC. HPLC elution profiles demonstrated that the IV sulfate formulation at pH 6.9–7.0 was stable at 60° C. for 19 days, with the generation of trace degradation products visible at 70° C. at 19 days. The relative amounts of these degradation products was observed to increase as a function of incubation temperature between 70° C. and 90° C.

Long-term stability prediction is based on an assumption that a ten fold increase in temperature roughly corresponds to a stability increase of ten fold in time at lower temperatures. Obtained data indicate that 20 mg/ml isotonic pH 6.9–7.0 colistin formulations will be stable at room temperature in excess of 5 years.

EXAMPLE 17

Jet Nebulization Characteristics of Pre-formulated Colistin and Colimycin Aerosol Formulations This example describes nebulization of colimycin and colistin component IV for aerosol formulations.

Colimycin was freshly dissolved in 37.5 mM (isotonic) NaCl at a concentration of 20 mg (colistin base equivalents)/ml solution immediately prior to nebulization. Colistin component IV sulfate or hydrochloride formulations were as described above in Example 15.

Four ml of solution to be nebulized was placed in a Pari LC Jet nebulizer fitted with a Pulmonaide Compressor, DeVilbiss Model 5650D, with an air flow rate of 4–6 liters/minute. Aerosol generated was characterized by passing through a Malvern Mastersizer X laser diffraction particle analyzer. Each formulation was analyzed multiple times to determine reproducibility of results, which were expressed as total obscuration time, mass median particle diameter, and respirable fraction.

Mass median particle diameters were expressed as average ±standard deviation (n) for aerosols.

Average respirable fractions were calculated as average percentage of particles ranging from 1 micron to 6 microns in diameter within the aerosol over time.

What is claimed:

1. A formulation for treatment and prevention of *Pseudomonas aeruginosa* or *Stenotrophomonas maltophilia* infections comprising a substantially pure colistin component selected from the group consisting of colistin component I, III and IV depicted by the general formula

[chemical structure showing cyclic peptide with $H_2N$, $R_1$, $R_2$, $CH_3$, $NH_2$, $OH$ groups]

wherein $R_1$ is 6-methylheptanoyl and $R_2$ is isopropyl (colistin component I), $R_1$ is 6-methyloctanoyl and $R_2$ is secondary butyl (colistin component III), $R_1$ is 6-methyloctanoyl and $R_2$ is isopropyl (colistin component IV);

a mixture thereof or a pharmaceutically acceptable salt thereof in a dry powder form or in a solution.

2. The formulation of claim 1 wherein the concentration of the colistin component, the mixture thereof or the salt thereof is from about 1 to about 50 mg/ml.

3. The formulation of claim 2 wherein the concentration of the colistin component, the mixture thereof or the salt thereof is from about 2 to about 20 mg/ml.

4. The formulation of claim 1 comprising from about 5 to about 250 mg of the colistin component, the mixture or salt thereof administered twice daily.

5. The formulation of claim 4 having pH between 4.0 and 7.5.

6. The formulation of claim 5 having pH between 6.5 and 7.5.

7. The formulation of claim 6 administered in an aerosol or in a dry powder form.

8. The formulation of claim 7 wherein the colistin component, the mixture or the salt thereof is milled into a dry powder.

9. The formulation of claim 8 wherein the dry powder has particle sizes predominantly between about 1 and about 5 microns.

10. The formulation of claim 9 wherein the dry powder is delivered by a dry powder inhaler or by a metered dose inhaler.

11. The formulation of claim 7 wherein the colistin component, the mixture or the salt thereof is formulated as a solution for aerosolization.

12. The formulation of claim 11 wherein, upon aerosolization, the aerosol has particle sizes between about 1 and about 5 microns.

13. The formulation of claim 12 wherein the aerosol is delivered by a jet or ultrasonic nebulizer.

14. The formulation of claim 13 wherein the purified colistin component is dissolved in an aqueous solvent to form an isotonic solution.

15. The formulation of claim 14 wherein the colistin component is dissolved in saline.

16. The formulation of claim 14 wherein the colistin component is dissolved in saline having a concentration ranging from about 0.45% to about 0.9 percent.

17. The formulation of claim 7 wherein the pharmaceutically acceptable salt of the colistin component is selected from the group consisting of an acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, sulfate, succinate, tannate, tartrate, teoclate, tosylate, triethiodide and valerate.

18. The formulation of claim 17 wherein the pharmaceutically acceptable salt is chloride, hydrochloride, phosphate, sulfate, acetate, lactate or gluconate.

19. The formulation of claim 18 wherein the colistin component is formulated as sulfate or hydrochloride.

20. The formulation of claim 18 wherein the colistin component is the colistin component IV formulated as a sulfate or hydrochloride salt.

21. The formulation of claim 18 wherein the colistin component is the colistin component I formulated as a sulfate or hydrochloride salt.

22. The formulation of claim 18 wherein the colistin component is the colistin component III formulated as a sulfate or hydrochloride salt.

23. The formulation of claim 20 wherein the colistin component IV is formulated as sulfate salt.

24. An anti-*Pseudomonas aeruginosa* agent which is a substantially pure colistin component selected from the group consisting of colistin component I, II, III and IV, a mixture thereof or a pharmaceutically acceptable salt thereof in a dry powder form or in a solution.

25. The agent of claim 24 administered in amount from about 2 to about 250 mg twice daily.

26. The agent of claim 25 administered in amount from about 4 to about 100 mg twice daily.

27. The agent of claim 25 in the dry powder form.

28. The agent of claim 27 milled into the dry powder having particle sizes between about 1 and about 5 microns.

29. The agent of claim 28 delivered by a dry powder inhaler or by a metered dose inhaler.

30. The agent of claim 26 formulated as a solution for aerosolization.

31. The agent of claim 30 forming, upon aerosolization, particle sizes predominantly between about 1 and about 5 microns.

32. The agent of claim 31 delivered by a jet or ultrasonic nebulizer.

33. The agent of claim 25 dissolved in an aqueous solvent for aerosolization.

34. The agent of claim 33 dissolved in an aqueous solvent to form an isotonic solution.

35. The agent of claim 33 dissolved in a saline having a concentration ranging from about 0.45 about 0.9 percent.

36. The agent of claim 24 formulated as the pharmaceutically acceptable salt selected from the group consisting of acetate, benzenesulfonate, benzoate, bicarbonate, bisulfate, bitartrate, borate, bromide, calcium edetate, camsylate, carbonates, chloride, clavulanate, citrates, dihydrochlorides, edetates, edisylates, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, sulfate tannate, tartrate, teoclate, tosylate, triethiodide and valerate.

37. The agent of claim 36 formulated as a chloride, hydrochloride, phosphate, sulfate, acetate, lactate or gluconate salt.

38. The agent of claim 37 formulated as the sulfate or hydrochloride salt.

39. The agent of claim 37 which is the colistin component I, III or IV sulfate or hydrochloride salt.

40. An anti-*Pseudomonas aeruginosa* agent which is a colistin component I having a general formula

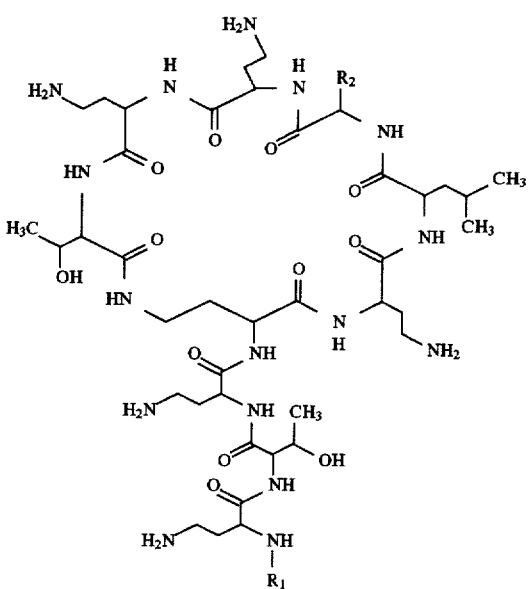

wherein R₁ is 6-methylheptanoyl and R₂ is isobutyl, said agent further having the following characteristics:

UV absorbance is maximized at 210 to 220 nm;

optical polarization is levorotary –46°; and $^{13}$C nuclear magnetic resonance spectra: (ppm in D₂O): 175.81, 175.65, 175.54, 175.08, 174.97, 174.30, 69.88, 69.31, 68.97, 62.57, 62.54, 61.93, 56.09, 55.96, 55.93, 55.01, 54.97, 54.66, 54.61, 54.56, 54.53, 54.49, 54.36, 54.21, 54.17, 54.06, 53.78, 53.65, 39.59, 39.48, 39.40, 39.33, 39.31, 38.38, 31.54, 31.51, 31.47, 31.40, 31.20, 31.08, 29.92, 28.92, 28.27, 27.38, 27.32, 27.26, 25.17, 24.73, 24.68, 23.98, 23.24, 23.18, 22.04, 21.67;

or a pharmaceutically acceptable salt thereof.

41. An anti-*pseudomonas aeruginosa* agent which is a colistin component IV having a general formula

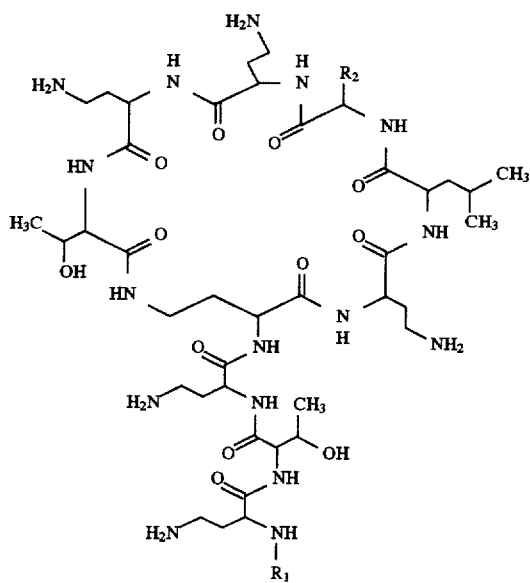

wherein R₁ is 6-methyloctanoyl and R₂ is isopropyl, said agent further having the following characteristics:

UV absorbance is maximized at 210 to 220 nm;

optical polarization is levorotary –47°; and $^{13}$C nuclear magnetic resonance spectra: (ppm in D₂O): 180.33, 177.66, 177.32, 176.07, 175.73, 175.58, 175.51, 175.04, 174.93, 174.58, 174.23, 69.78, 69.15, 62.41, 61.78, 55.97, 55.8, 54.78, 54.55, 54.4, 54.03, 53.91, 53.58, 42.48, 41.81, 39.42, 39.23, 39.14, 38.82, 38.26, 38.11, 36.3, 33.33, 32.46, 31.58, 31.46, 31.4, 31.07, 31.03, 28.54, 28.28, 27.19, 27.14, 25.11, 24.55, 23.83, 22.99, 21.94, 21.55, 21.34, 13.36;

or a pharmaceutically acceptable salt thereof.

42. An anti-*Pseudomonas aeruginosa* agent which is a colistin component III having a general formula

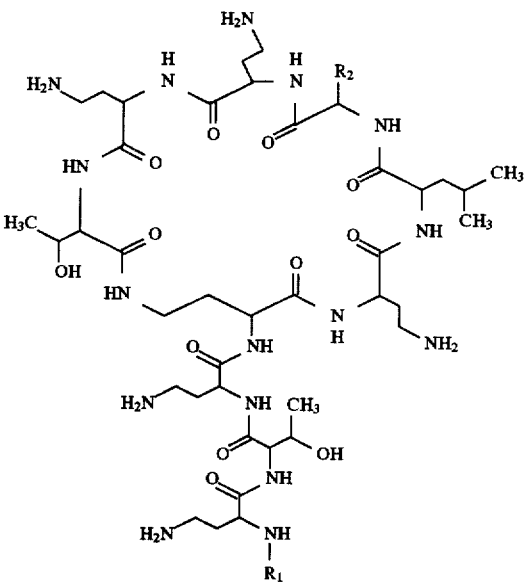

wherein R₁ is 6-methyloctanoyl and R₂ is sec-butyl, said agent further having the following characteristics:

UV absorbance is maximized at 210 to 220 nm;

optical polarization is levorotary –42°; and $^{13}$C nuclear magnetic resonance spectra: (ppm in D₂O): 177.64, 177.30, 177.19, 175.76, 175.60, 175.25, 175.04, 174.99, 174.81, 174.65, 174.27, 69.87, 69.49, 62.60, 61.92, 55.79, 54.91, 54.64, 54.59, 54.37, 54.19, 54.07, 53.86, 53.82, 39.63, 39.43, 39.32, 38.38, 38.22, 36.41, 31.65, 31.48, 28.67, 28.33, 27.32, 27.25, 25.13, 24.75, 24.68, 23.97, 23.78, 22.04, 21.98, 21.65, 21.44, 18.11, 13.40, 13.06;

or a pharmaceutically acceptable salt thereof.

* * * * *

UNITED STATES PATENT AND TRADEMARK OFFICE
CERTIFICATE OF CORRECTION

PATENT NO. : 5,767,068
DATED : JUNE 16, 1998
INVENTOR(S) : VanDeVanter, et al.

It is certified that error appears in the above-identified patent and that said Letters Patent is hereby corrected as shown below:

Column 8, line 23, delete "isopropyl" and insert --isobutyl--;

Column 13, line 18, delete "$(C_{53}H_{100}N_{16}Na_5O28S_5)$" and insert --$(C_{58}H_{105}N_{16}Na_5O_{28}S_5)$--;

Column 13, line 19, delete "$(C_{53}H_{100}ON_{16}O_{13})$" and insert --$(C_{53}H_{100}N_{16}O_{13})$--;

Column 13, line 59, delete "PH" and insert --pH--;

Column 30, line 17, delete "$C_{53}H_{118}N_{16}O_3OS_3$" and insert --$C_{53}H_{116}N_{16}O_{30}S_3$--;

Column 34, line 61, delete "isopropyl" and insert --isobutyl--;

Column 34, line 64, delete "isopropyl" and insert --isobutyl--;

Column 38, line 1, delete "isopropyl" and insert --isobutyl--.

Signed and Sealed this

Third Day of August, 1999

Attest:

Q. TODD DICKINSON

*Attesting Officer*         *Acting Commissioner of Patents and Trademarks*